(12) United States Patent
Veidman et al.

(10) Patent No.: US 11,682,118 B2
(45) Date of Patent: *Jun. 20, 2023

(54) SYSTEMS AND METHODS FOR ANALYSIS OF TISSUE IMAGES

(71) Applicant: Nucleai Ltd, Tel-Aviv (IL)

(72) Inventors: Avi Veidman, Gedera (IL); Lotan Chorev, Tel-Aviv (IL)

(73) Assignee: Nucleai Ltd, Tel-Aviv (IL)

( * ) Notice: Subject to any disclaimer, the term of this patent is extended or adjusted under 35 U.S.C. 154(b) by 0 days.

This patent is subject to a terminal disclaimer.

(21) Appl. No.: 17/542,605

(22) Filed: Dec. 6, 2021

(65) Prior Publication Data
US 2022/0092781 A1 Mar. 24, 2022

Related U.S. Application Data

(63) Continuation of application No. 16/635,206, filed as application No. PCT/IL2018/050862 on Aug. 2, 2018, now Pat. No. 11,195,274.

(Continued)

(51) Int. Cl.
*G06K 9/00* (2022.01)
*G06T 7/11* (2017.01)
(Continued)

(52) U.S. Cl.
CPC ............ *G06T 7/11* (2017.01); *G06F 18/2415* (2023.01); *G06N 3/08* (2013.01); *G06T 7/0012* (2013.01);
(Continued)

(58) Field of Classification Search
None
See application file for complete search history.

(56) References Cited

U.S. PATENT DOCUMENTS

| 10,049,450 B2 | 8/2018 | Madabhushi et al. |
| 10,235,755 B2 | 3/2019 | Madabhushi et al. |

(Continued)

FOREIGN PATENT DOCUMENTS

| WO | WO 2016/075096 | 5/2016 |
| WO | WO 2016/087592 | 6/2016 |
| WO | WO 2016/154116 | 9/2016 |

OTHER PUBLICATIONS

Communication Pursuant to Article 94(3) EPC dated Mar. 11, 2022 From the European Patent Office Re. Application No. 18759763.8. (11 Pages).

(Continued)

*Primary Examiner* — Soo Jin Park

(57) ABSTRACT

There is provided a method of computing at least one slide-level tissue type for a tissue image of tissue extracted from a patient, comprising: receiving a tissue image of a slide including tissue extracted from the patient, segmenting tissue objects of the tissue image, creating a tissue image patches from the segmented tissue objects of the tissue image, classifying, by a patch-level classifier, each of the plurality of tissue image patches into at least one patch-level tissue type, wherein each of the classified tissue image patches is associated with a relative location within the tissue image, analyzing, by a slide-level analysis code, the classified at least one patch-level tissue type and associated relative location for each of the plurality of tissue image patches outputted by the patch-level classifier, for computing at least one slide-level tissue type for the tissue image, and providing the at least one slide-level tissue type.

20 Claims, 11 Drawing Sheets

Related U.S. Application Data

(60) Provisional application No. 62/540,652, filed on Aug. 3, 2017.

(51) Int. Cl.

| | | |
|---|---|---|
| *G16H 10/40* | (2018.01) | |
| *G16H 50/20* | (2018.01) | |
| *G06N 3/08* | (2023.01) | |
| *G06T 7/00* | (2017.01) | |
| *G06V 10/50* | (2022.01) | |
| *G06F 18/2415* | (2023.01) | |
| *G06V 20/69* | (2022.01) | |
| *G16H 15/00* | (2018.01) | |

(52) U.S. Cl.
CPC .............. *G06V 10/50* (2022.01); *G06V 20/69* (2022.01); *G16H 10/40* (2018.01); *G16H 50/20* (2018.01); *G06T 2200/24* (2013.01); *G06T 2207/20021* (2013.01); *G06T 2207/20076* (2013.01); *G06T 2207/20081* (2013.01); *G06T 2207/20084* (2013.01); *G06T 2207/30024* (2013.01); *G16H 15/00* (2018.01)

(56) References Cited

U.S. PATENT DOCUMENTS

| | | |
|---|---|---|
| 2008/0082468 A1 | 4/2008 | Long et al. |
| 2008/0273788 A1 | 11/2008 | Soenksen et al. |
| 2020/0066407 A1 | 2/2020 | Stumpe et al. |
| 2020/0372635 A1 | 11/2020 | Veidman et al. |

OTHER PUBLICATIONS

International Preliminary Report on Patentability dated Feb. 13, 2020 From the International Bureau of WIPO Re. Application No. PCT/IL2018/050862. (17 Pages).

International Search Report and the Written Opinion dated Mar. 29, 2019 From the International Searching Authority Re. Application No. PCT/IL2018/050862. (27 Pages).

Invitation to Pay Additional Fees, Communication Relating to the Results of the Partial International Search and the Provisional Opinion dated Nov. 23, 2018 From the International Searching Authority Re. Application No. PCT/IL2018/050862. (17 Pages).

Notice of Allowance dated Jul. 21, 2021 from the US Patent and Trademark Office Re. U.S. Appl. No. 16/635,206. (13 pages).

Bautista et al. "Digital Staining for Histopathology Multispectral Images by the Combined Application of Spectral Enhancement and Spectral Transformation", 33rd Annual International Conference of the IEEE EMBS, Engineering in Medicine and Biology Society 2011, XP032320540, Boston, MA, USA, Aug. 30-Sep. 3, 2011, p. 8013-8016, Aug. 30, 2011. Abstract.

Hou et al. "Patch-Based Convolutional Neural Network for whole Slide Tissue Image Classification", Proceedings of the IEEE Conference on Computer Vision and Pattern Recognition, CVPR 2016, XP055523985, Las Vegas, Nevada, USA, Jun. 27-30, 2016, p. 2424-2433, Jun. 27, 2016. Figs.1, 2, Sections 2, 4.

Kong et al. "Cancer Metastasis Detection via Spatially Structured Deep Network", International Conference on Simulation, Modeling, and Programming for Autonomous Robots, SIMPAR 2017, XP047416155, LNCS 10265: 236-248, Published Online May 23, 2017. Abstract, Sections 2.1, 2.3, 2.4, 3.1, Fig.2.

Niwas et al. "An Expert Support System for Breast Cancer Diagnosis Using Color Wavelet Features", Journal of Medical Systems, XP055569508, 36(5): 3091-3102, Published Online Oct. 18, 2011.

Ramos et al. "Image Colour Segmentation by Genetic Algorithms", Proceedings of the 11th Portuguese Conference on Pattern Recognition, RecPad '2000, Porto, Portugal, May 11-12, 2000, XP055569512, p. 125-129, Dec. 17, 2004.

Sinha et al. "Improved Brain Tumor Detection With Ontology", International Journal of Computational Engineering Research, XP055569532, 2(2): 584-588, Mar.-Apr. 2012.

Wang et al. "Deep Learning for Identifying Metastatic Breast Cancer", ArXiv: 1606.05718v1 [q-bio.QM], XP055568296, p. 1-6, Jun. 18, 2016.

Office Action dated Aug. 16, 2022 From the Israel Patent Office Re. Application No. 272433. (4 Pages).

SYSTEMS AND METHODS FOR ANALYSIS OF TISSUE IMAGES

RELATED APPLICATIONS

This application is a continuation of U.S. patent application Ser. No. 16/635,206 filed on Jan. 30, 2020, which is a National Phase of PCT Patent Application No. PCT/IL2018/050862 having International filing date of Aug. 2, 2018, which claims the benefit of priority under 35 USC § 119(e) of U.S. Provisional Patent Application No. 62/540,652 filed on Aug. 3, 2017. The contents of the above applications are all incorporated by reference as if fully set forth herein in their entirety.

FIELD AND BACKGROUND OF THE INVENTION

The present invention, in some embodiments thereof, relates to image processing and, more specifically, but not exclusively, to systems and methods for classification of images including tissue samples.

A pathology report produced after reviewing a patient's biological tissue samples is often the gold standard in the diagnosis of many diseases. Most pathologist reviewed samples using a traditional microscope. Digital pathology is the process by which histology and cytology slides are digitized to produce high resolution images.

SUMMARY OF THE INVENTION

According to a first aspect, a computer implemented method of computing at least one slide-level tissue type for a tissue image of tissue extracted from a patient, comprises: receiving a tissue image of a slide including tissue extracted from the patient, segmenting tissue objects of the tissue image, creating a plurality of tissue image patches from the segmented tissue objects of the tissue image, classifying, by a patch-level classifier, each of the plurality of tissue image patches into at least one patch-level tissue type, wherein each of the classified tissue image patches is associated with a relative location within the tissue image, analyzing, by a slide-level analysis code, the classified at least one patch-level tissue type and associated relative location for each of the plurality of tissue image patches outputted by the patch-level classifier, for computing at least one slide-level tissue type for the tissue image, and providing the at least one slide-level tissue type.

According to a second aspect, a system for computing at least one slide-level tissue type for a tissue image of tissue extracted from a patient, comprises: a non-transitory memory having stored thereon a code for execution by at least one hardware processor, the code comprising: code for receiving a tissue image of a slide including tissue extracted from the patient, code for segmenting tissue objects of the tissue image, code for creating a plurality of tissue image patches from the segmented tissue objects of the tissue image, code for classifying, by a patch-level classifier, each of the plurality of tissue image patches into at least one patch-level tissue type, wherein each of the classified tissue image patches is associated with a relative location within the tissue image, code for analyzing, by a slide-level analysis code, the classified at least one patch-level tissue type and associated relative location for each of the plurality of tissue image patches outputted by the patch-level classifier, for computing at least one slide-level tissue type for the tissue image, and code for outputting the at least one slide-level tissue type.

According to a third aspect, a computer program product for computing at least one slide-level tissue type for a tissue image of tissue extracted from a patient, comprises: a non-transitory memory having stored thereon a code for execution by at least one hardware processor, the code comprising instructions for: receiving a tissue image of a slide including tissue extracted from the patient, segmenting tissue objects of the tissue image, creating a plurality of tissue image patches from the segmented tissue objects of the tissue image, classifying, by a patch-level classifier, each of the plurality of tissue image patches into at least one patch-level tissue type, wherein each of the classified tissue image patches is associated with a relative location within the tissue image, analyzing, by a slide-level analysis code, the classified at least one patch-level tissue type and associated relative location for each of the plurality of tissue image patches outputted by the patch-level classifier, for computing at least one slide-level tissue type for the tissue image, and outputting the at least one slide-level tissue type.

At least some systems, methods, apparatus, and/or code instructions described herein improve the technology of automated analysis of tissue images, by analyzing as a whole, the tissue image of the slide including tissue extracted from a patient. Such tissue images may include a large amount of data, which may indicate a large number of different tissue objects, for example, bacteria, target tissue that was biopsied which may be for example normal or malignant, and additional cells such as immune system cells. Moreover, the imaged tissue has been extracted from the body of the patient, making correlation to other nearby anatomies difficult or impossible. For example, a chest CT slice may be analyzed by knowledge of where each organ is located to other organs, which is constant in patients having normal anatomies. In contrast, tissue extracted from an organ via biopsy, or cytology samples of fluids of the body, are taken out of context of the body of the patient, and cannot be analyzed relative to the normal known anatomical structure of the rest of the body of the patient. At least some systems, methods, apparatus, and/or code instructions described herein integrate patch level analysis to obtain a slide level outcome, for example, an overall indication for the tissue image as a whole.

At least some systems, methods, apparatus, and/or code instructions described herein improve the medical field of analyzing images of tissue samples. Using standard methods, a pathologist manually examines tissue sample, or images of tissue samples, and performs a manual analysis. Such manual analysis is subjective, based on the individual pathologist looking at the tissue sample. Two different pathologists looking at the same tissue sample may providing differing analysis opinions, which may even contradict each other. The automated analysis of images of tissue samples by at least some systems, methods, apparatus, and/or code instructions described herein is not based on a simple coding of an existing manual process onto a computer. Rather, at least some systems, methods, apparatus, and/or code instructions described herein turn a subjective method into an objective, reproducible method based on trained artificial intelligence code, such as neural networks and/or other classification methods. Inventors developed new steps that did not previously exist in the manual process, and do have not counterparts in the manual process, namely, training of the artificial intelligence code and/or machine learning code (e.g., neural network, classifier), and/or execution of the trained artificial intelligence code and/or machine learning code to perform the automated analysis of the image of the tissue sample. At least the trained artificial intelligence code and/or machine learning code described herein provides objective, reproducible analysis results, which are not available using standard manual processes. At least some systems, methods, apparatus, and/or code instructions described herein improve the medical field of treating a patient, specifically in terms of obtaining a biopsy from the patient and/or resection of cancerous tumor(s) from the patient. The biopsy procedure and/or resection of tumor may be dynamically guided intraoperatively, and on-site (i.e., within the operating room), to improve medical outcomes and/or medical procedure results according to the automated analysis of the image of the tissue samples performed by the analysis code described herein. The improvement includes, for example:

Objective, reproducible, rapid, on-site feedback regarding the tissue/cells extracted from the patient during the medical procedure and adequacy of the sample. For example, medical centers relying on manual analysis of obtained tissue samples do not have the human resources to have a specialist trained in analysis in the procedure room (e.g., cytologist, cyto-technician) as the procedure to obtain the tissue is taking place.

Generation of instructions for additional treatment when the tissue image crated according to the obtained sample fails to meet a set of rules defining adequacy of the treatment. The instructions may be presented, for example, within the GUI, as audio played over speakers, as text, as a video, as an email, as a pop-up, and/or may be code instructions for execution by a surgical robot.

Increased procedure yield rate, resulting in lower rates of repeat procedures and/or lower rates of re-admission.

Relatively improved resection of tumors with clean margins. Masses, such as tumors, which may be malignant or benign, are resected in certain medical procedures. The success of such operations is affected by the ability of the surgeon to remove the cancerous and/or malignant tissue and obtain clean surgical margins. Intraoperative analysis of surgical margins may be automatically performed by the code described herein. The resected tumor and/or cells obtained from the resected area may be processed intraoperatively, for example, with a frozen section method, and digitized to create the image that is automatically analyzed as described herein, and/or for example, slide digitization may be performed by a camera mounted on a microscope, a slide scanner, and/or a spectral imager. Inadequate surgical margins may be corrected based on the analysis outcome indicating unclean margins. Analysis resulting indicative of clean margins may trigger a halt to the resection procedure, potentially preventing additional resection of tissue that might otherwise occur without the analysis results.

Improved biopsy results capturing sufficient tissue suitable for analysis. Various techniques are used for biopsies. For example, fine needle aspiration (FNA) is a method to sample cells of a suspected mass or a fluid. FNA procedures are considered less traumatic than other types of biopsies. Examples for common FNA biopsies are: Thyroid, Lung and breast biopsies. Another common type biopsy is a core needle biopsy (CNB) which is used to take out pieces of tissue from the suspected area. Examples for CNB usage are prostate and breast biopsies. The tissue sample is digitized to create the image for analysis. Optionally, a frozen section is prepared from the tissue, and the image is created based on the frozen section. The image of the sampled cells is automatically analyzed by code as described herein to determine the nature of the biopsied region, for example, to check the cellular content and/or adequacy of FNA smears and/or biopsy touch imprints, during the biopsy procedure. The results outputted by the analysis code may be provided (e.g., presented on a display of a client terminal) intraoperatively for guiding the biopsy, for example, to obtain additional samples when insufficient and/or inadequate tissue has been obtained, or to prevent repeating the biopsy procedure when the obtained sample is determined to be sufficient and/or adequate by the analysis code.

Improvement of operation of a robot performing the biopsy and/or tumor resection. The robot may be operated manually, automatically, or semi-automatically, Instructions for performing additional biopsy and/or tumor resection may be automatically generated based on the automated analysis of the image of the tissue. The instructions may be code instructions for execution by the robotic surgical instrument that automatically performs the procedure, and/or manual instructions for the user performing the procedure using the robot. The instructions may be, for example, to stop the biopsy and/or resection procedure when the tissue sample is determined to be adequate by the analysis code, or to perform another biopsy and/or perform additional resection when the tissue sample is determined to be inadequate by the analysis code.

At least some systems, methods, apparatus, and/or code instructions described herein improve the accuracy of trained segmentation code and/or classifiers (e.g., CNN) for classifying and/or segmenting patches of tissue images. The accuracy of the trained classifier and/or segmentation code is improved by using both tissue images that are annotated at the slide-level (without being annotated at the pixel element level), and tissue images that include pixel level annotations, without requiring performing pixel level annotation on the tissue images that have slide level-annotation.

It is noted that automated analysis of images of tissue samples extracted from the patient (e.g., histology, cytology) is different than analysis of anatomical images captured of the patient (e.g., CT, MRI, x-ray, ultrasound). For example, in most cases in pathology, the tissue portion viewed and scanned is a small part of the biopsy. The biopsy in some cases does not include the entire region of interest (e.g., tumor, organ). In addition, each patch extracted from the tissue image is associated with its own tissue portion which does not necessarily appear in other patches (e.g., apart from overlapping regions of the patches), enabling independent analysis of each respective patch. However, to obtain a final slid-level diagnoses (also referred to herein as slide-level tissue type), a full slide analysis based on the analysis performed on each patch is performed, as described herein. For example, in the same single tissue image of the same slide, there may be several patches that classify to the same patch-level tissue type. In contrast, in anatomical images, usually an entire body part is imaged (e.g., chest, abdomen, limb, head), and the analysis is performed for something specific that requires viewing the entire image and/or image set in the case of 3D imaging such as CT that generates slices of images. For example, the analysis is to detect a tumor which may look like a dot on an x-ray. Therefore, the processing and analysis of tissue images is different than the processing and analysis of anatomical images. In another example, an image of a scanned pathology slide is equivalent in terms of pixels and/or data size to approximately 1000 x-ray images, or about 500 or about 2000 or about 5000 x-ray images. When multiple slides are created (e.g., sequentially cut from the target tissue, obtained from multiple biopsies, of different stains), the amount of data is much larger. Moreover, when the data from the multiple slides is aggregated into 3D volumetric data, the data of the 3D tissue image is much larger than other 3D datasets, such as CT scans and MRI scans. The large amount of data in the tissue images cannot be analyzed using methods developed for analyzing images with much smaller data such as x-ray images, where the x-ray image as a whole may be fed into a classifier.

In a further implementation form of the first, second, and third aspects, the at least one slide-level tissue type is distinct from the at least one patch-level tissue type.

In a further implementation form of the first, second, and third aspects, the at least one slide-level tissue type is computed based on two or more distinct patch level tissue types computed for two or more patches.

In a further implementation form of the first, second, and third aspects, the at least one slide-level tissue type is computed according to at least one geometric feature based on associated relative location of each of the plurality of tissue patches.

In a further implementation form of the first, second, and third aspects, the at least one geometric feature is selected from the group consisting of: distance between patches, total area of patches of a same patch-level tissue type, area of patches of a same patch-level tissue type directly neighboring one another, patches of a first patch level-tissue type separated by at least one patch of a second patch level-tissue type, density of tissue objects identified in at least one patch, relative angle between patches according to a center point, and combinations of the aforementioned.

In a further implementation form of the first, second, and third aspects, the associated relative location is according to location of patches of the extracted tissue located on the slide, and excludes relative in-situ anatomical locations within the body of the patient.

In a further implementation form of the first, second, and third aspects, the method further comprises and/or the system further comprises code instructions for and/or the computer program product further comprises additional instructions for generating instructions for treatment of the patient according to a set of rules applied to the analysis.

In a further implementation form of the first, second, and third aspects, the instructions for treatment of the patient comprise instructions to obtain another tissue sample from the patient, and further comprising iterating the acts of the method for analysis of the another tissue for generating updated instructions for treatment of the patient.

In a further implementation form of the first, second, and third aspects, the instructions for treatment of the patient are presented in a graphical user interface (GUI), and wherein the GUI is updated according to updated instructions.

In a further implementation form of the first, second, and third aspects, the set of rules is indicative of adequacy of the tissue image.

In a further implementation form of the first, second, and third aspects, when the set of rules is not met the generated instructions include instructions for additional treatment of the patient.

In a further implementation form of the first, second, and third aspects, the set of rules for generating instructions to obtain another tissue sample include: blurry tissue image, poor sample preparation, unclean margins and instructions to cut additional tissue, identified tissue does not correspond to target biopsy location, insufficient tissue for proper classification, and no malignancy detected.

In a further implementation form of the first, second, and third aspects, when the set of rules is met the instructions include instructions to stop the treatment.

In a further implementation form of the first, second, and third aspects, the slide-level analysis code comprises at least one CNN trained according to a training dataset comprising a plurality of training tissue images each including a respective indication of slide-level tissue type, a plurality of tissue images patches each classified into at least one tissue type and associated with a relative location of the respective tissue image patch within the respective training tissue image.

In a further implementation form of the first, second, and third aspects, the slide-level analysis code comprises a set of rules selected according to a received indication.

In a further implementation form of the first, second, and third aspects, the received indication is selected from the group consisting of: organ from which tissue is extracted, fluid sample that includes the extracted tissue, clinical procedure used to extract the tissue, clinical indication performed to obtain the extracted tissue.

In a further implementation form of the first, second, and third aspects, the slide-level analysis code comprises: computing a probability heatmap, wherein each pixel of the heatmap corresponds to a certain patch of plurality of tissue image patches and includes a respective value indicative of the patch-level tissue type of the corresponding tissue image patch selected from the group consisting of: a vector storing plurality of probabilities each probability indicative of the respective patch being classified to one of a plurality of possible patch-level tissue types, and a single indication of one of a plurality of possible patch-level issue types associated with each patch, extracting features from the probability heatmap according to a plurality of feature thresholds, computing a respective binary mask of a plurality of binary masks, according to features extracted according to each feature threshold of the plurality of feature thresholds, extracting geometrical features from each respective binary mask of the plurality of binary masks, and computing the at least one slide-level tissue type according to the extracted geometrical features of each respective binary mask.

In a further implementation form of the first, second, and third aspects, features extracted from the probability heatmap and geometrical features extracted from binary masks are selected from the group consisting of: size of a largest connected area in the mask and/or heatmap, eccentricity of the largest connected area in the mask and/or heatmap, solidity of the largest connected area in the mask and/or heatmap, extent of the largest connected area in the mask and/or heatmap, number of pixels above a pixel threshold, distance between largest connected areas, and combinations of the aforementioned.

In a further implementation form of the first, second, and third aspects, the plurality of feature thresholds are selected according to values of heat pixels corresponding to respective patch-level tissue types.

In a further implementation form of the first, second, and third aspects, the slide-level analysis code comprises: computing, for each pixel element of each patch of the plurality of tissue image patches, a pixel element level segmentation including a probability of the respective pixel element being associated with the at least one patch-level tissue type, extracting geometrical features according to the pixel element level segmentation of each patch, wherein the geometrical features are computed based on relative locations of at least two segmented pixels of at least two patches, and computing the at least one slide-level tissue type according to the extracted geometrical features.

In a further implementation form of the first, second, and third aspects, a plurality of tissue images of a plurality of slides of sequential sections of the tissue extracted from the patient are received, wherein the plurality of tissue images are registered to compute a single registered tissue image, wherein values of pixels of the single registered tissue image are computed according to values of pixels of the registered tissue images, wherein the segmenting, the creating the plurality of tissue image patches, the classifying, the analyzing, and the providing are performed for the single registered tissue image for computing at least one multi-slide level tissue type.

In a further implementation form of the first, second, and third aspects, a plurality of tissue images of a plurality of slides of the tissue extracted from the patient are received, wherein the segmenting, the creating the plurality of tissue image patches, the classifying, the analyzing, and the providing are performed for the single registered tissue image for computing at least one multi-slide level tissue type.

In a further implementation form of the first, second, and third aspects, a plurality of tissue images of a plurality of slides of sequential sections of the tissue extracted from the patient are received, wherein each of the plurality of slides is stained with a different staining type, wherein the segmenting, the creating the plurality of tissue image patches, the classifying, the analyzing, and the providing are performed for each of the plurality of tissue images, and further comprising computing at least one multi-level tissue type according to an analysis based on a set of rules for each tissue image of the plurality of tissue images.

In a further implementation form of the first, second, and third aspects, the tissue image is of a whole slide including a plurality of tissue regions and non-tissue background.

In a further implementation form of the first, second, and third aspects, segmenting tissue objects comprises computing at least one of: a binary mask indicative of tissue objects of the tissue image, and polygons denoting tissue objects of the tissue image.

In a further implementation form of the first, second, and third aspects, segmenting tissue objects comprises: excluding non-tissue background of the tissue image according to a color of pixels of the tissue image indicative of non-tissue background, to obtain a set of pixels indicative of tissue objects, converting the set of pixels indicative of tissue objects to a selected color space according to a resolution of the tissue image, clustering the set of converted pixels indicative of tissue objects according to the selected color space to computed a plurality of clusters, computing a color distance between a respective location of a respective cluster of the plurality of clusters within a plane of the selected color space, and a defined configuration of colors of the selected color space, and defining pixels of clusters having color distance above a pre-defined distance threshold as non-tissue.

In a further implementation form of the first, second, and third aspects, segmenting tissue objects comprises identifying pixels indicative of non-tissue background of the tissue image, and dilating identified pixels indicative of non-tissue background surrounded by pixels indicative of tissue for defining the identified pixels as tissue.

In a further implementation form of the first, second, and third aspects, segmenting tissue objects comprises: dividing the tissue image into a plurality of tissue image patches, identifying a sub-set of the plurality of tissue image patches as indicative of out-of-focus by a trained classifier that receives as input each of the plurality of tissue image patches and outputs a corresponding out-of-focus indication, and removing the sub-set of the plurality of tissue image patches indicative of out-of-focus from the plurality of tissue image patches to create a set of remaining in-focus patches, and outputting the set of remaining in-focus patches for classifying by the patch-level classifier.

In a further implementation form of the first, second, and third aspects, the method further comprises and/or the system further comprises code instructions for and/or the computer program product further comprises additional instructions for computing an indication of an amount of the out-of-focus of the sub-set of the plurality of tissue image patches, and when the indication of the amount of the out-of-focus is above an out-of-focus threshold, at least one of: stopping execution of the method prior to classifying by the patch-level classifier, and presenting instructions on a display to re-scan a slide with tissue to generate another tissue image.

In a further implementation form of the first, second, and third aspects, the tissue image of the slide including tissue extracted from the patient is performed using a multispectral imager that creates tissues images with at least 4 spectrum frequencies.

In a further implementation form of the first, second, and third aspects, the slide-level analysis code computes the at least one slide-level tissue type according to an analysis of an estimated amount of tissue objects detected in the plurality of patches of the tissue image.

In a further implementation form of the first, second, and third aspects, the slide-level analysis code computes the at least one slide-level tissue type according to a set of rules denoting a threshold of the classified at least one tissue patch of the plurality of image patches, wherein the at least one slide-level tissue type is computed for the classified at least one tissue patch of the plurality of image patches above the threshold.

In a further implementation form of the first, second, and third aspects, the patch-level classifier outputs, for each respective patch, a vector storing plurality of probabilities, each probability indicative of the respective patch being classified to one of a plurality of possible patch-level tissue types.

In a further implementation form of the first, second, and third aspects, the patch-level classifier outputs, for each respective patch, a single indication of one of a plurality of possible patch-level tissue types.

In a further implementation form of the first, second, and third aspects, the slide-level analysis code comprises a convolutional neural network (CNN) that receives as input each respective vector outputted by the patch-level classifier for each of the plurality of patches of the tissue image.

In a further implementation form of the first, second, and third aspects, the method further comprises and/or the system further comprises code instructions for and/or the computer program product further comprises additional instructions for aggregating the plurality of image patches into a single aggregated image, and classifying the single aggregated image by the slide-level analysis code.

In a further implementation form of the first, second, and third aspects, the method further comprises and/or the system further comprises code instructions for and/or the computer program product further comprises additional instructions for detecting tissue objects of a certain tissue type in the tissue image.

In a further implementation form of the first, second, and third aspects, detecting is performed according to at least one of: at least one patch of the plurality of patches classified as the certain tissue type, and segmenting of tissue objects of the certain tissue type, above a predefined threshold number of pixels of the tissue image segmented as the certain tissue type.

In a further implementation form of the first, second, and third aspects, the method further comprises and/or the system further comprises code instructions for and/or the computer program product further comprises additional instructions for receiving a selected patch of the plurality of patches, computing an encoding for the selected patch by an autoencoder CNN, identifying at least one similar patch from a dataset of patch encodings, according to a requirement of a similarity distance between the encoding of the selected patch and an encoding of the at least one similar patch, selecting at least one matching similar patch from the identified at least one similar patch according to a match between at least one patch-level tissue type of the identified at least one similar patch and the at least one patch-level tissue type of the selected patch, and presenting the selected at least one matching similar patch in the GUI.

In a further implementation form of the first, second, and third aspects, the autoencoder CNN is trained on a plurality of patches extracted from each of a plurality of tissue images labeled with a ground-truth at least one patch-level tissue type, according to a loss function denoting a reconstruction error between respective patches of the plurality of patches and a corresponding decoding of the respective patches.

In a further implementation form of the first, second, and third aspects, the method further comprises and/or the system further comprises code instructions for and/or the computer program product further comprises additional instructions for computing an encoding by an autoencoder CNN, for each patch of the plurality of patches of the tissue image, computing a statistical distance between each encoding of each patch and a dataset storing encodings of patches denoting normal tissue, and identifying at least one patch of the plurality of patches as abnormal when the statistical distance between the respective patch and at least one nearest encoding of patches denoting normal tissue is above an abnormality threshold.

In a further implementation form of the first, second, and third aspects, the dataset stores cluster centroids computed for a plurality of clusters of the encodings of the patches denoting normal tissue, wherein the statistical distance is computed between the encoding of each patch and the cluster centroids.

In a further implementation form of the first, second, and third aspects, the method further comprises and/or the system further comprises code instructions for and/or the computer program product further comprises additional instructions for computing an encoding by an autoencoder CNN, for each patch of the plurality of patches of the tissue image, clustering the encodings of the plurality of patches into at least one cluster, wherein each cluster is associated with a cluster center, computing a statistical distance between each encoding of each patch and the cluster center of the cluster associated with the respective patch, and identifying at least one patch of the plurality of patches as abnormal when the statistical distance between the encoding of the respective patch and the cluster center is above an abnormality threshold.

In a further implementation form of the first, second, and third aspects, the method further comprises and/or the system further comprises code instructions for and/or the computer program product further comprises additional instructions for iteratively inputting each respective patch of the plurality of patches into a trained patch classification CNN for computing a probability of likelihood of at least one patch-level tissue type, wherein at least one neuron is randomly dropped during each iteration, and computing an indication of abnormality for the respective patch when an analysis of the probability of likelihood of at least one patch-level tissue type varies between iterations according to a consistency requirement, wherein the trained patch classification CNN is trained according to patches labeled with patch-level tissue type.

In a further implementation form of the first, second, and third aspects, the method further comprises and/or the system further comprises code instructions for and/or the computer program product further comprises additional instructions for receiving a manual diagnosis of the tissue, and generating an alert when a mismatch is detected by an automated comparison of the manual diagnosis to the computed at least one slide-level tissue type.

In a further implementation form of the first, second, and third aspects, the method further comprises and/or the system further comprises code instructions for and/or the computer program product further comprises additional instructions for training the patch-level classifier, by: providing a training dataset including a plurality of tissue images obtained for a plurality of sample individuals, wherein the plurality of tissue images include a first sub-set of slide-level annotated images comprising at least one slide-level tissue type, and a second sub-set of pixel element level annotated images comprising at least one pixel element level tissue type, training a pixel element level CNN implementation of the patch-level classifier according to the second sub-set of pixel element level annotated images, and further training the pixel element level CNN implementation of the patch-level classifier according to patches created from of images of the first sub-set of slide-level annotated images, and according to a loss function based on distance to a certain patch of the plurality of patches associated with highest probability of belonging to the at least one slide-level tissue type of the tissue image associated with the certain patch.

In a further implementation form of the first, second, and third aspects, initial probabilities of belonging to the at least one slide-level tissue type of the tissue image associated with the certain patch is computed by the trained pixel element level CNN, wherein the initial probabilities are adjusted according to the loss function.

In a further implementation form of the first, second, and third aspects, the patch-level classifier comprises a CNN trained according to a first sub-set of slide-level annotated images comprising at least one slide-level tissue type, and a second sub-set of pixel element level annotated images comprising at least one pixel element level tissue type, wherein a ground truth is indicated according to a location of a respective patch of the second sub-set including the at least one pixel element level tissue type, and according to the slide-level tissue type of the first sub-set wherein only patches with highest probability above a threshold indicative as belonging to the slide-level tissue type according to the CNN are considered.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1:
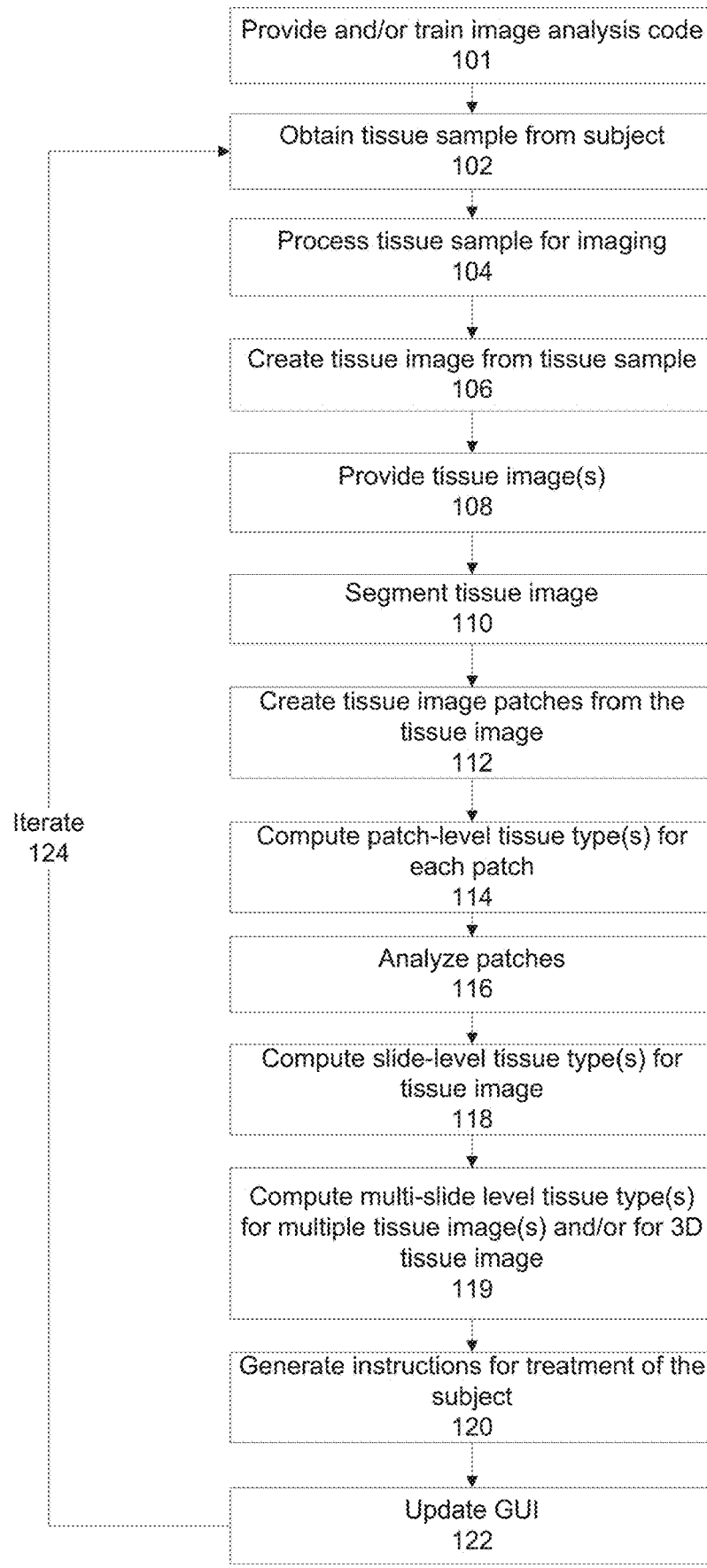
FIG. 1 is a is a flowchart of a method of computing slide-level tissue type(s) for a tissue image of tissue extracted from a patient, in accordance with some embodiments of the present invention.

The present invention, in some embodiments thereof, relates to image processing and, more specifically, but not exclusively, to systems and methods for classification of pathological images.

As used herein, the term tissue, for example, as used with reference to tissue image, tissue sample, and tissue extracted from a subject, refers to a physically connected group of cells such as histological sample, for example, as obtained by a biopsy of an organ such as thyroid, and/or refers to individual cells or small clumps of cells such as a cytology sample, obtained from for example, a sample of fluid such as urine, cerebrospinal fluid, and/or scrapping of tissue suspended within an artificial fluid.

As used herein, the term slide-level tissue type may refer, for example, to a diagnosis made for the patient according to the tissue image created from the tissue sample extracted from the patient (optionally arranged on a slide). The diagnosis may be, for example, according to a set of predefined available diagnosis, optionally according to a diagnostic coding system. The term slide-level tissue type may sometimes be interchanged with the term slide-level indication, or slide-level diagnosis.

As used herein, the term multi-slide tissue type may refer, for example, to a diagnosis made for the patient according to an analysis of multiple slides, which may=including the same target tissue (e.g., organ, tumor) and/or target fluid (e.g., multiple slides created from the same fluid sample) and/or of the same region (e.g., created from multiple biopsies of the same target tissue and/or organ). For example, slides depicting sequential cuts (e.g., as made in a frozen section), and/or different stains (e.g., each slide is of a different stain) and/or of different biopsies from different regions of the same target tissue and/or target organ. The multi-slide tissue type may be computed according to slide-level tissue types of multiple slides, and/or according to patch-level tissue types of multiple patches from multiple different slides. The diagnosis may be, for example, according to a set of predefined available diagnosis, optionally according to a diagnostic coding system. The term multi-slide level tissue type may sometimes be interchanged with the term multi-slide level indication, or multi-slide level diagnosis.

The multi-slide analysis based on multiple sequential slides may be according to three dimensional (3D) data, for example, stored as voxels, and/or as two dimensional (2D) pixel slices. The multi-slide level analysis may be computed as described with reference to the slide level analysis, adapted for multiple slides.

At least some of the systems, methods, apparatus, and/or code instructions described herein may analyze 3D volumetric data of a 3D tissue image and/or created by aggregating data from sequential 2D slices.

An aspect of some embodiments of the present invention relates to systems, methods, an apparatus, and/or code instructions (i.e., stored in a data storage device, executable by one or more hardware processor) for computing an indication of one or more slide-level tissue types computed for a tissue image of tissue image extracted from a patient, for example, by biopsy, by fine need aspiration, by sampling of body fluid, and/or by surgery. Tissue object(s) of the tissue image may be segmented, optionally removing background and/or noise from the tissue image. Tissue image patches are created from the segmented tissue object(s) of the tissue image. Each tissue image patch is classified by a patch-level classifier into one or more patch-level tissue types. Each of the classified image patches is associated with a relative location within the tissue image. The patch level tissue type(s) and associated relative locations of the patches are analyzed by slide-level analysis code, optionally, a trained convolutional neural network (CNN). The slide-level analysis code computes the slide-level tissue type(s) for the tissue image according to the analysis.

Optionally, a multi-slide level tissue type(s) is computed according to multiple tissue images (e.g., sequential slices of tissue, and/or obtained by different biopsies of the tissue) and/or according to multiple patches of the multiple tissue images, based on the patch-level tissue type(s) and/or slide-level tissue type(s), and/or based on relative location(s) of the patches and/or tissue images.

Optionally, the slide-level tissue type is distinct from the patch-level tissue type. For example, the patch-level tissue type is indicative of findings at the respective patch, which the slide-level tissue type provides an overall diagnosis for the slide as a whole. For example, one patch-level tissue type is of Bacteria Type A. Another patch-level tissue type is of immune system cells Type B. The slide-level tissue type is computed to be a diagnosis of C. Optionally, the multi-slide level tissue type is distinct from the slide-level tissue type and/or the patch-level tissue type.

Optionally, the slide-level tissue type is computed based on two or more distinct patch level tissue types computed for two or more patches. Alternatively or additionally, the multi-level tissue type is computed based on two or more distinct slide level tissue types computed for two or slides patches and/or based on two or more distinct patch level tissue types computed for two or more patches which may be from different slides.

Optionally, the slide-level tissue type is computed according to geometric feature(s) based on associated relative location of each of the tissue patches and/or slides and/or tissues patches of different slides. Exemplary geometric features include: distance between patches, distance between slides, distance between patches of slides, total area of patches of a same patch-level tissue type of the same slide and/or of different slides, area of patches of a same patch-level tissue type directly neighboring one another of the same slide and/or of different slides, patches of a first patch level-tissue type separated by at least one patch of a second patch level-tissue type of the same slide and/or of different slides, density of tissue objects identified in at least one patch of the same slide and/or of different slides, relative angle between patches of the same slide and/or of different slides according to a center point, and combinations of the aforementioned.

Optionally, the associated relative location is according to location of patches of the extracted tissue located on the slide. The relative location excludes relative in-situ anatomical locations within the body of the patient. For example, in standard body imaging (e.g., x-ray, CT, MRI), the organs are at the same general location for most patients with normal anatomies. In contrast, once tissue is extracted from the body, and imaged to create the tissue image, the relative location is for the patches and/or tissue objects of the tissue sample, and have nothing to do with relative locations within the body.

At least some systems, methods, apparatus, and/or code instructions described herein improve the technology of automated analysis of tissue images, by analyzing as a whole, the tissue image of the slide including tissue extracted from a patient. Such tissue images may include a large amount of data, which may indicate a large number of different tissue objects, for example, bacteria, target tissue that was biopsied which may be for example normal or malignant, and additional cells such as immune system cells. Moreover, the imaged tissue has been extracted from the body of the patient, making correlation to other nearby anatomies difficult or impossible. For example, a chest CT slice may be analyzed by knowledge of where each organ is located to other organs, which is constant in patients having normal anatomies. In contrast, tissue extracted from an organ via biopsy, or cytology samples of fluids of the body, are taken out of context of the body of the patient, and cannot be analyzed relative to the normal known anatomical structure of the rest of the body of the patient. At least some systems, methods, apparatus, and/or code instructions described herein integrate patch level analysis to obtain a slide level outcome, for example, an overall indication for the tissue image as a whole.

At least some systems, methods, apparatus, and/or code instructions described herein improve the medical field of analyzing images of tissue samples. Using standard methods, a pathologist manually examines tissue sample, or images of tissue samples, and performs a manual analysis. Such manual analysis is subjective, based on the individual pathologist looking at the tissue sample. Two different pathologists looking at the same tissue sample may providing differing analysis opinions, which may even contradict each other. The automated analysis of images of tissue samples by at least some systems, methods, apparatus, and/or code instructions described herein is not based on a simple coding of an existing manual process onto a computer. Rather, at least some systems, methods, apparatus, and/or code instructions described herein turn a subjective method into an objective, reproducible method based on trained artificial intelligence code, such as neural networks and/or other classification methods. Inventors developed new steps that did not previously exist in the manual process, and do have not counterparts in the manual process, namely, training of the artificial intelligence code and/or machine learning code (e.g., neural network, classifier), and/or execution of the trained artificial intelligence code and/or machine learning code to perform the automated analysis of the image of the tissue sample. At least the trained artificial intelligence code and/or machine learning code described herein provides objective, reproducible analysis results, which are not available using standard manual processes.

At least some systems, methods, apparatus, and/or code instructions described herein improve the medical field of treating a patient, specifically in terms of obtaining a biopsy from the patient and/or resection of cancerous tumor(s) from the patient. The biopsy procedure and/or resection of tumor may be dynamically guided intra-operatively, and on-site (i.e., within the operating room), to improve medical outcomes and/or medical procedure results according to the automated analysis of the image of the tissue samples performed by the analysis code described herein. The improvement includes, for example:

Objective, reproducible, rapid, on-site feedback regarding the tissue/cells extracted from the patient during the medical procedure and adequacy of the sample. For example, medical centers relying on manual analysis of obtained tissue samples do not have the human resources to have a specialist trained in analysis in the procedure room (e.g., cytologist, cyto-technician) as the procedure to obtain the tissue is taking place.

Generation of instructions for additional treatment when the tissue image crated according to the obtained sample fails to meet a set of rules defining adequacy of the treatment. The instructions may be presented, for example, within the GUI, as audio played over speakers, as text, as a video, as an email, as a pop-up, and/or may be code instructions for execution by a surgical robot.

Increased procedure yield rate, resulting in lower rates of repeat procedures and/or lower rates of re-admission.

Relatively improved resection of tumors with clean margins. Masses, such as tumors, which may be malignant or benign, are resected in certain medical procedures. The success of such operations is affected by the ability of the surgeon to remove the cancerous and/or malignant tissue and obtain clean surgical margins. Intraoperative analysis of surgical margins may be automatically performed by the code described herein. The resected tumor and/or cells obtained from the resected area may be processed intraoperatively, for example, with a frozen section method, and digitized to create the image that is automatically analyzed as described herein, and/or for example, slide digitization may be performed by a camera mounted on a microscope, a slide scanner, and/or a spectral imager. Inadequate surgical margins may be corrected based on the analysis outcome indicating unclean margins. Analysis resulting indicative of clean margins may trigger a halt to the resection procedure, potentially preventing additional resection of tissue that might otherwise occur without the analysis results.

Improved biopsy results capturing sufficient tissue suitable for analysis. Various techniques are used for biopsies. For example, fine needle aspiration (FNA) is a method to sample cells of a suspected mass or a fluid. FNA procedures are considered less traumatic than other types of biopsies. Examples for common FNA biopsies are: Thyroid, Lung and breast biopsies. Another common type biopsy is a core needle biopsy (CNB) which is used to take out pieces of tissue from the suspected area. Examples for CNB usage are prostate and breast biopsies. The tissue sample is digitized to create the image for analysis. Optionally, a frozen section is prepared from the tissue, and the image is created based on the frozen section. The image of the sampled cells is automatically analyzed by code as described herein to determine the nature of the biopsied region, for example, to check the cellular content and/or adequacy of FNA smears and/or biopsy touch imprints, during the biopsy procedure. The results outputted by the analysis code may be provided (e.g., presented on a display of a client terminal) intraoperatively for guiding the biopsy, for example, to obtain additional samples when insufficient and/or inadequate tissue has been obtained, or to prevent repeating the biopsy procedure when the obtained sample is determined to be sufficient and/or adequate by the analysis code.

Improvement of operation of a robot performing the biopsy and/or tumor resection. The robot may be operated manually, automatically, or semi-automatically, Instructions for performing additional biopsy and/or tumor resection may be automatically generated based on the automated analysis of the image of the tissue. The instructions may be code instructions for execution by the robotic surgical instrument that automatically performs the procedure, and/or manual instructions for the user performing the procedure using the robot. The instructions may be, for example, to stop the biopsy and/or resection procedure when the tissue sample is determined to be adequate by the analysis code, or to perform another biopsy and/or perform additional resection when the tissue sample is determined to be inadequate by the analysis code.

At least some systems, methods, apparatus, and/or code instructions described herein improve the accuracy of trained segmentation code and/or classifiers (e.g., CNN) for classifying and/or segmenting patches of tissue images. The accuracy of the trained classifier and/or segmentation code is improved by using both tissue images that are annotated at the slide-level (without being annotated at the pixel element level), and tissue images that include pixel level annotations, without requiring performing pixel level annotation on the tissue images that have slide level-annotation.

It is noted that automated analysis of images of tissue samples extracted from the patient (e.g., histology, cytology) is different than analysis of anatomical images captured of the patient (e.g., CT, MRI, x-ray, ultrasound). For example, in most cases in pathology, the tissue portion viewed and scanned is a small part of the biopsy. The biopsy in some cases does not include the entire region of interest (e.g., tumor, organ). In addition, each patch extracted from the tissue image is associated with its own tissue portion which does not necessarily appear in other patches (e.g., apart from overlapping regions of the patches), enabling independent analysis of each respective patch. However, to obtain a final slid-level diagnoses (also referred to herein as slide-level tissue type), a full slide analysis based on the analysis performed on each patch is performed, as described herein. For example, in the same single tissue image of the same slide, there may be several patches that classify to the same patch-level tissue type. In contrast, in anatomical images, usually an entire body part is imaged (e.g., chest, abdomen, limb, head), and the analysis is performed for something specific that requires viewing the entire image and/or image set in the case of 3D imaging such as CT that generates slices of images. For example, the analysis is to detect a tumor which may look like a dot on an x-ray. Therefore, the processing and analysis of tissue images is different than the processing and analysis of anatomical images. In another example, an image of a scanned pathology slide is equivalent in terms of pixels and/or data size to approximately 1000 x-ray images, or about 500 or about 2000 or about 5000 x-ray images. When multiple slides are created (e.g., sequentially cut from the target tissue, obtained from multiple biopsies, of different stains), the amount of data is much larger. Moreover, when the data from the multiple slides is aggregated into 3D volumetric data, the data of the 3D tissue image is much larger than other 3D datasets, such as CT scans and MRI scans. The large amount of data in the tissue images cannot be analyzed using methods developed for analyzing images with much smaller data such as x-ray images, where the x-ray image as a whole may be fed into a classifier.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 2:
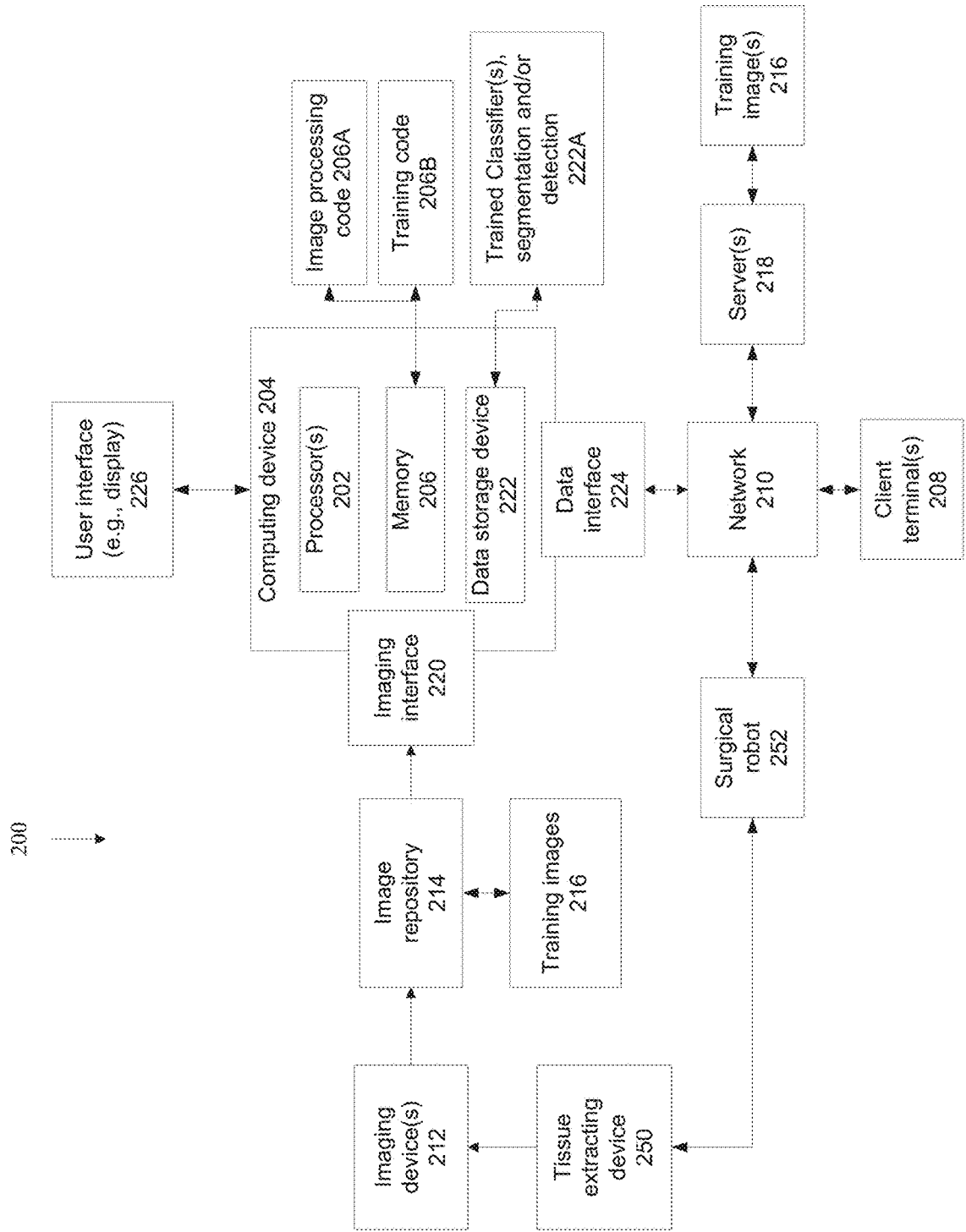
FIG. 2 is a is a block diagram of components of a system for computing slide-level tissue type(s) for a tissue image of tissue extracted from a patient and/or for training one or more classifiers for analysis of the tissue image, in accordance with some embodiments of the present invention.
Figure 3:
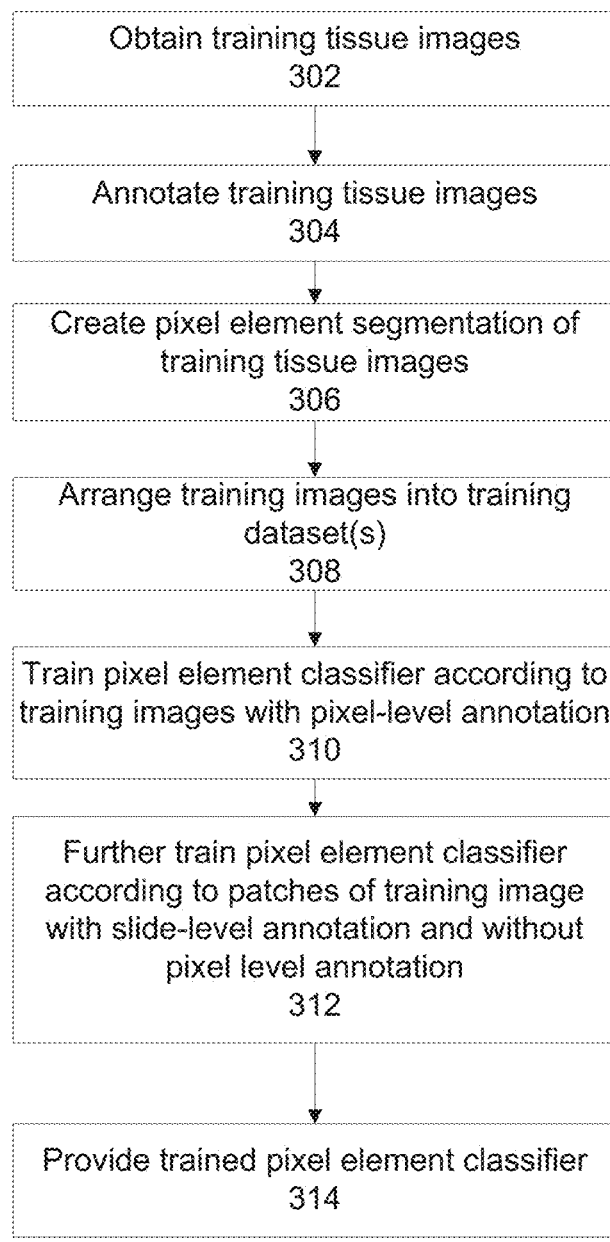
FIG. 3 is a flowchart of an exemplary method for training a classifier for computing pixel element segmentation of a tissue image and/or patch(es) of the tissue image, in accordance with some embodiments of the present invention.
Figure 4:
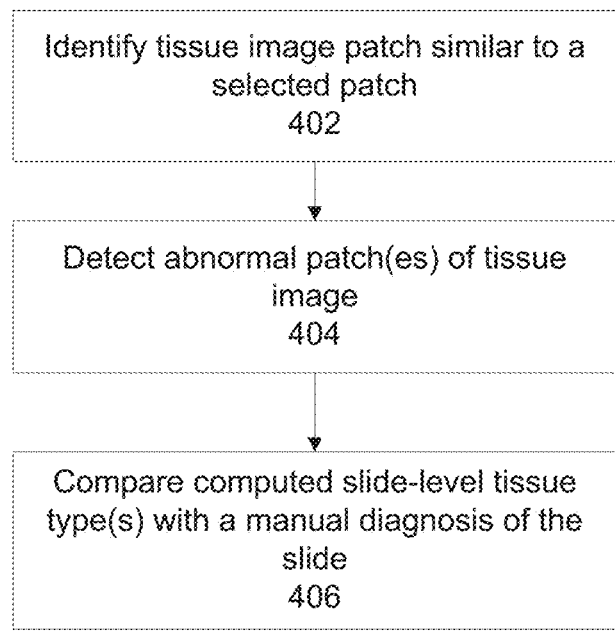
FIG. 4 is a flowchart of some exemplary optional features of the method described with reference to FIG. 1, in accordance with some embodiments of the present invention.

Reference is now made to FIG. 1, which is a flowchart of a method of computing slide-level tissue type(s) for a tissue image of tissue extracted from a patient, in accordance with some embodiments of the present invention. Reference is also made to FIG. 2, which is a block diagram of components of a system 200 for computing slide-level tissue type(s) for a tissue image of tissue extracted from a patient and/or for training one or more classifiers for analysis of the tissue image, in accordance with some embodiments of the present invention. Reference is also made to FIG. 3, which is a flowchart of an exemplary method for training a classifier for computing pixel element segmentation of a tissue image and/or patch(es) of the tissue image, in accordance with some embodiments of the present invention. Reference is also made to FIG. 4, which is a flowchart of some exemplary optional features of the method described with reference to FIG. 1, in accordance with some embodiments of the present invention. System 200 may implement the acts of the method described with reference to FIG. 1 and/or FIG. 3, optionally by a hardware processor(s) 202 of a computing device 204 executing code instructions stored in a memory 206.

Computing device 204 may be implemented as, for example, a client terminal, a server, a virtual server, a laboratory workstation (e.g., pathology workstation), a procedure (e.g., operating) room computer and/or server, a virtual machine, a computing cloud, a mobile device, a desktop computer, a thin client, a Smartphone, a Tablet computer, a laptop computer, a wearable computer, glasses computer, and a watch computer. Computing 204 may include an advanced visualization workstation that sometimes is implemented as an add-on to a laboratory workstation and/or other devices for presenting indications of the analyzed tissue images and/or other computer added detections to the user (e.g. pathologist, interventional radiologist, oncologist, surgeon).

Computing device 204 may include locally stored software that performs one or more of the acts described with reference to FIG. 1 and/or FIG. 3 and/or FIG. 4, and/or may act as one or more servers (e.g., network server, web server, a computing cloud, virtual server) that provides services (e.g., one or more of the acts described with reference to FIG. 1 and/or FIG. 3 and/or FIG. 4) to one or more client terminals 208 (e.g., remotely located laboratory workstations, remote picture archiving and communication system (PACS) server, remote electronic medical record (EMR) server, remote tissue image storage server, remotely located operating room computing device) over a network 210, for example, providing software as a service (SaaS) to the client terminal(s) 208, providing an application for local download to the client terminal(s) 208, as an add-on to a web browser and/or a tissue imaging viewer application, and/or providing functions using a remote access session to the client terminals 208, such as through a web browser.

Is it noted that the training of the neural network, and the analysis of tissue images by the trained neural network, may be implemented by the same computing device 204, and/or by different computing devices 204, for example, one computing device trains the neural network, and transmits the trained neural network to a server device for analysis of tissue images.

Computing device 204 receives 2D tissue images captured by an imaging device(s) 212. Exemplary imaging device(s) 212 include: a scanner scanning in standard color channels (e.g., red, green blue), a multispectral imager acquiring images in four or more channels, a confocal microscope, and/or other imaging devices as described herein, a black a white imaging device, an imaging sensor.

Imaging device(s) 212 creates tissue images from physical tissue samples obtained by a tissue extracting device 250, for example, a fine needle for performing FNA, a larger bore needle for performing a core biopsy, and a cutting tool (e.g., knife, scissors, scoop) for cutting out a sample of the tissue (e.g., tumor removal).

Imaging device(s) 212 may create two dimensional tissue images.

Tissue extracting device 250 may be operated by a surgical robot 252, and/or manually by a user (e.g., physician, radiologist, oncologist, surgeon). Surgical robot 252 may be operated automatically, manually, and/or semi-automatically.

In some embodiments, surgical robot 252 operates tissue extracting device 250 to obtain additional tissue for generating additional tissue images by imaging device(s) 212, according to instructions generated by computing device 202 in response to analyzing previously obtained tissue images, as described herein.

Tissue images captured by imaging machine 212 may be stored in an image repository 214, for example, a storage server, a computing cloud, virtual memory, and a hard disk. Training images 216 may be created based on the captured tissue images, as described herein.

Training images 216 are used to train one or more of the classifiers (optionally CNNs), as described herein. It is noted that training images 216 may be stored by a server 218, accessibly by computing device 204 over network 210, for example, a publicly available training dataset, tissue images stored in a PACS server and/or pathology imaging server, and/or a customized training dataset created for training the classifiers, as described herein.

Computing device 204 may receive the training images 216 and/or tissue images from imaging device 212 and/or image repository 214 using one or more imaging interfaces 220, for example, a wire connection (e.g., physical port), a wireless connection (e.g., antenna), a local bus, a port for connection of a data storage device, a network interface card, other physical interface implementations, and/or virtual interfaces (e.g., software interface, virtual private network (VPN) connection, application programming interface (API), software development kit (SDK)).

Hardware processor(s) 202 may be implemented, for example, as a central processing unit(s) (CPU), a graphics processing unit(s) (GPU), field programmable gate array(s) (FPGA), digital signal processor(s) (DSP), and application specific integrated circuit(s) (ASIC). Processor(s) 202 may include one or more processors (homogenous or heterogeneous), which may be arranged for parallel processing, as clusters and/or as one or more multi core processing units.

Memory 206 (also referred to herein as a program store, and/or data storage device) stores code instruction for execution by hardware processor(s) 202, for example, a random access memory (RAM), read-only memory (ROM), and/or a storage device, for example, non-volatile memory, magnetic media, semiconductor memory devices, hard drive, removable storage, and optical media (e.g., DVD, CD-ROM). Memory 206 stores code instructions for implementing trained classifiers, detection code, and/or segmentation code 222A. Memory 206 stores image processing code 206A that implements one or more acts and/or features of the method described with reference to FIG. 1 and/or FIG. 4, and/or training code 206B that executes one or more acts of the method described with reference to FIG. 3.

Computing device 204 may include a data storage device 222 for storing data, for example, one or more trained classifiers, detection code, and/or segmentation code 222A (as described herein), and/or training images 216. Data storage device 222 may be implemented as, for example, a memory, a local hard-drive, a removable storage device, an optical disk, a storage device, and/or as a remote server and/or computing cloud (e.g., accessed over network 210). It is noted that trained classifiers, detection code, and/or segmentation code 222A, and/or training images 216 may be stored in data storage device 222, with executing portions loaded into memory 206 for execution by processor(s) 202.

Computing device 204 may include data interface 224, optionally a network interface, for connecting to network 210, for example, one or more of, a network interface card, a wireless interface to connect to a wireless network, a physical interface for connecting to a cable for network connectivity, a virtual interface implemented in software, network communication software providing higher layers of network connectivity, and/or other implementations. Computing device 204 may access one or more remote servers 218 using network 210, for example, to download updated training images 216 and/or to download an updated version of image processing code 206A, training code 206B, and/or the trained classifiers, detection code, and/or segmentation code 222A.

Computing device 204 may communicate using network 210 (or another communication channel, such as through a direct link (e.g., cable, wireless) and/or indirect link (e.g., via an intermediary computing device such as a server, and/or via a storage device) with one or more of:

- Surgical robot 252, for example, when computing device 204 generates instructions for operating surgical robot 252 in response to an analysis of the tissue image(s). The instructions may be code instructions for automatic operation of surgical robot 252, and/or manual instructions for manual operation of surgical robot 252.
- Client terminal(s) 208, for example, when computing device 204 acts as a server providing image analysis services (e.g., SaaS) to remote laboratory terminals, for analyzing remotely obtained tissue images.
- Server 218, for example, implemented in association with a PACS, which may storage large numbers of tissue images for analysis, for example, captured by an imaging machine of a pathology lab.
- Tissue image repository 214 that stores training images 216 and/or tissue images outputted by imaging device 212.

It is noted that imaging interface 220 and data interface 224 may exist as two independent interfaces (e.g., two network ports), as two virtual interfaces on a common physical interface (e.g., virtual networks on a common network port), and/or integrated into a single interface (e.g., network interface).

Computing device 204 includes or is in communication with a user interface 226 that includes a mechanism designed for a user to enter data (e.g., patient data) and/or view the computed analysis (e.g., slide-level tissue type(s), and/or view the segmentation(s), heatmaps, automatically generated reports, and/or other results as described herein. Exemplary user interfaces 226 include, for example, one or more of, a touchscreen, a display, a keyboard, a mouse, and voice activated software using speakers and microphone.

Referring now back to FIG. 1, at 101, image analysis code, including one or more of: classifier code, and/or detection code, and/or segmentation code is provided and/or trained.

Multiple instances of the image analysis code may be trained. Each instance of the image analysis code may be trained to process a certain type of tissue image, for example, according to one or more of the following: medical procedure being performed, image colors, image resolution, tissue type expected to be included in the tissue image, histology or cytology, and clinical indication.

The instances of the image analysis code may be selected from multiple available types of image analysis code. The selection may be performed manually by the user (e.g., via the GUI, for example, via a menu and/or icons of available image analysis code). The selection may be performed automatically by code that analyzes, for example, the tissue image, metadata of the image, and/or other patient data associated with the image such as procedure being performed (e.g., obtained from a PACS server, DICOM data, and/or electronic medical record).

The types of image analysis code may be implemented as, for example, neural network (NN), such as fully connected NN, convolutional NN, full convolutional NN, and/or a combination of multiple sub-architectures, for example, integrated networks, parallel networks, and/or cascade networks. Some image analysis code may output intermediate results, for example, a heatmap, which other types of image analysis codes may process further. In some implementations, other machine learning methods may be used, for example, support vector machine, clusterization methods, sets of rules, and decision trees.

An exemplary method of training the image analysis code is described with reference to FIG. 3.

At 102, tissue is obtained. The tissue may be obtained intra-operatively, during for example, a biopsy procedure, a FNA procedure, a core biopsy procedure, colonoscopy for removal of colon polyps, surgery for removal of an unknown mass, surgery for removal of a benign cancer, and/or surgery for removal of a malignant cancer. Tissue may be obtained from fluid, for example, urine, synovial fluid, blood, and cerebral spinal fluid.

Tissue may be obtained by using the tissue extracting device.

Tissue may be obtained by the surgical robot operating the tissue extracting device.

Tissue may be in the form of a connected group of cells, for example, a histological slide. Tissue may be in the form of individual or clumps of cells suspended within a fluid, for example, a cytological sample.

At 104, tissue is processed for imaging. Optionally, the tissue image created from the physical slide with tissue thereon is a color image, optionally including multiple channels for each pixel, for example, 3 (e.g., RGB) or more channels (e.g., multispectral, confocal). Optionally, the tissue image is created based on visible light energy. For example, capturing a digital image of a view as seen under a light microscope.

The tissue may be arranged on a slide. A frozen section may be created and sliced for creating multiple slides. Tissue may be stained.

The slides may include histology slides and/or cytology slides.

The tissue may be chemically stained for increased visibility for generation of the tissue image. The staining process takes additional time. In some implementations, the tissue itself is not stained, but rather imaging methods are used that do not necessarily requiring staining, for example, a spectral imager.

Optionally, a set of colors associated with the chemical staining and/or virtual staining (e.g., by a multispectral imager) is identified. The set of colors may be stored, for example, in a dataset according to the chemical staining and/or virtual staining. The set of colors may be automatically identified by code and/or manually designated by the user according to the chemical and/or virtual staining. The identified set of colors may be used for segmenting tissue versus non-tissue background, and/or for selecting the type of image analysis code, as described herein in additional detail. The identified set of colors may be stored, for example, in a LAB color space, RGB color space, and/or other color spaces. It is noted that LAB color space is more linear than RGB color space.

At 106, a tissue image is created by imaging the tissue by the imaging device. Optionally, slides including the prepared tissue are imaged by the imaging device.

Optionally, the tissue slides are imaged at high magnification, for example, between about X200-X400, or about X100-400, or about X100-X200, or about X100, or about X200, or about X400, or other values. Such high magnification imaging may create very large images, for example, on the order of Giga Pixel sizes. Such large tissue images of the entire slide may be referred to herein as Whole Slide Images (WSI).

The imaging device may be implemented as, for example, a spectral imager, such as a multispectral (few to tens of channels) or a hyperspectral (up to hundreds of channels). The multispectral imager creates tissue images with 4 or more spectrum frequencies, which is noted to be higher than the 3 spectrums of a normal imager (e.g. imaging in red, green, and blue (RGB). The imager may produce a spectral signature including multiple channels for each pixel, in contrast for example, to the 3 channels (e.g., RGB) obtained by the traditional staining process. The image analysis code described herein may be created and/or trained according to the spectral signature of each pixel. It is noted that alternatively, a standard imager imaging in 3 channels (e.g., RGB) may be used, and/or a black and white imager may be used.

Alternatively or additionally, the image is implemented based on a Stimulated Raman scattering (SRS) microscopy. The spectral image (cube) acquired by a spectral imager, or a SRS microscope, may be analyzed by combining morphological based method with spectral based methods to improve the outcome of traditional image analysis methods relying purely on RGB images.

Alternatively or additionally, a mapping and/or other transformation function is estimated between the colors (e.g., RGB) of an image of stained tissue and the spectrum corresponding to the same location. The mapping may be used to produce a virtual stained slide from a spectral image of a fresh tissue slide.

At 108, the tissue image of the tissue extracted from the body of the patient is provided. Multiple tissue images of the tissue may be provided, for example, from the same biopsy, of different stains, of the same body fluid, and slices from a sequential slicing (e.g., frozen section). The multiple tissue images may be arranged as a single 3D tissue image, and/or as a set of 2D slices. The multi-slide level tissue type(s) may be computed according to an analysis of the multiple tissue images, as described herein.

The tissue images may be obtained, for example, from a PACS server, an EMR server, from the imaging device that captured the tissue image from the physical slide that included the tissue extracted from the patient, and/or from a storage device (e.g., portable storage medium, storage server). For example, tissue images are automatically sent to analysis after capture by the imager and/or once the images are stored after being scanned by the imager.

At 110, the tissue image, also referred to as the WSI, is segmented, for example, by segmentation code stored as code instructions in a memory executable by the hardware processor(s) of the computing device. The tissue image includes tissue portions indicative of the physical tissue obtained from the patient, and non-tissue background (e.g., empty space on the slide), and/or noise (e.g., color markers such as made by a pen, out-of-focus areas, dirt on the slide). It is noted that noise may be due to tissue which cannot be adequately analyzed, for example, out-of-focus areas, and/or may be due to non-tissue elements such as dirt.

The segmentation of the tissue is performed for segmenting tissue objects from the tissue image, for example, cells such as normal cells, cancer cells, pre-cancer cells, cells of the organ, immune system cells, and bacteria. The tissue objects represent portions of the tissue image for further analysis. The segmentation may be performed for exclusion of the background and/or noise.

It is noted that the segmentation step is optional, since the entire tissue image (i.e., WSI) may be processed. However, processing of the segmented tissue objects may increase computational efficiency of the computational device, by preventing processing of regions with irrelevant data and/or with no data (i.e., the background and/or noise). Processing of the segmented tissue objects may reduce errors, by avoiding incorrect processing of the irrelevant data.

The segmentation may be performed per pixel element (e.g., pixel), where each pixel of the image is segmented (e.g., into the tissue object(s)) or not segmented (i.e., denoting background and/or noise).

The segmentation may be performed by computing a binary mask indicative of the tissue objects of the tissue image, and/or polygons denoting the tissue objects of the tissue image. The binary mask may have the same size as the tissue image, where cells of binary mask having a value of 1 or TRUE denote corresponding segmented pixel elements. The polygons may include, for example, rectangles and/or other enclosed complex shapes that encompass the tissue object(s).

Optionally, segmentation is performed to identify tissue versus non-tissue. Alternatively or additionally, segmentation is performed to identify out-of-focus tissue for exclusion from further analysis.

The segmentation of the tissue image to differential between tissue objects and non-tissue background may be performed, for example, based on color segmentation, by segmentation code (e.g., trained CNN) that computes the segmentation, and/or based on detection code (e.g., trained CNN) that detects the tissue object(s).

An exemplary method for segmentation of tissue object(s) according to color is now described:

The set of colors associated with the chemical and/or virtual staining method is identified (e.g., as described herein).

A resolution may be selected for the segmentation. The resolution may be selected, for example, from a dataset storing different recommended resolutions, such as according to expected types of tissue objects. The resolution may vary according to a later processing phase.

Non-tissue background of the tissue image is excluded (e.g., removed) according to predefined color(s) of pixels of the tissue image indicative of non-tissue background, for example, white. The remaining pixels include tissue objects. It is noted that some image scanners provide an alpha channel that includes areas that were not scanned since no tissue was recognized at those areas. Such areas of the alpha channel are designated as non-tissue background.

The set of pixels indicative of tissue objects are converted to a selected color space according to a resolution of the tissue image. For example, converted to LAB color space.

The set of converted pixels are clustered. The clustering is performed according to colors in the selected color space. Clustering may be performed by clustering code.

A color distance is computed between a respective location of a respective cluster within a plane of the selected color space (e.g., cluster center), and a defined configuration of colors of the selected color space. The defined configuration of colors is according to the identified set of colors based on the chemical and/or virtual staining.

Pixels of clusters having color distance above a pre-defined distance threshold are designated as non-tissue. Alternatively or additionally, pixels of clusters having color distance below the pre-defined distance threshold are designated as tissue object(s).

When a higher resolution is required than was processed, the tissue image is split into multiple sub-parts each at the higher resolution, and the acts are iterated for the higher resolution.

Optionally, pixels indicative of non-tissue background, which are surrounded by pixels indicative of tissue object(s) are dilated and identified as tissue. Such pixels may appear as white pixels inside the tissue, for example, as "holes" in the tissue. Such pixels are considered as tissue, even when their color is the color of background, and/or when such pixels actually indicate non-tissue background. The dilation fills the small "holes" for further analysis.

An exemplary method for segmentation and/or detection of out-of-focus regions is now described:

Optionally, the tissue image is divided into patches. Each patch may be according to a predefined size (e.g., 256×256 pixels or other values) and/or predefined resolution and/or predefined overlap (e.g., 10%, 25%, 50%, or other overlap values). Alternatively, the tissue image as a whole is analyzed.

A sub-set of the tissue image patches and/or sub-regions of the whole tissue image and/or sub-regions of the patches are identified as indicative of out-of-focus. The identification may performed by a trained classifier, for example, a segmentation CNN that outputs segmentation regions of the patches and/or tissue image including out-of-focus regions, and/or a classification CNN that outputs whether an inputted image patch includes out-of-focus regions (and/or whether the entire patch is out-of-focus). Alternatively or additionally, the trained classifier identifies in-focus regions and/or patches, where the out-of-focus regions and/or patches are identified by exclusion of the in-focus regions and/or patches. The classifier is trained on whole tissue images and/or image patches and/or annotated tissue regions marked as out-of-focus. The out-of-focus regions may be due to errors in-focusing by lenses during capture of the tissue image, and/or the out-of-focus regions may be created by running filter(s) on in-focus tissue images to cause the out-of-focus effect.

The sub-set of the tissue image patches (and/or regions) indicative of out-of-focus are excluded from the tissue image patches, to create a set of remaining in-focus patches and/or regions. The out-of-focus patches may be united into a single out-of-focus patch. Overlapping patches and/or patches in proximity to one another may be grouped into a single patch.

The set of remaining in-focus patches is provided for further analysis. Alternatively or additionally, the single out-of-focus region is provided, and excluded from the tissue image to obtain in-focus patches. In another example, a binary mask is created based on the single out-of-focus region to exclude the out-of-focus areas of the tissue image.

Optionally, an indication of an amount of the out-of-focus is computed. Different measures of the extent of the patches being out-of-focus may be used. When the indication of the amount of being out-of-focus is above an out-of-focus threshold, the process may be stopped such that the out-of-focus patches are not classified by the patch-level classifier and/or none of the patches of the tissue image are classified. Instructions may be presented (e.g., within the GUI) to re-scan the slide to generate another tissue image. The re-scanning may be performed manually by the user and/or automatically by the imager.

Figure 5:
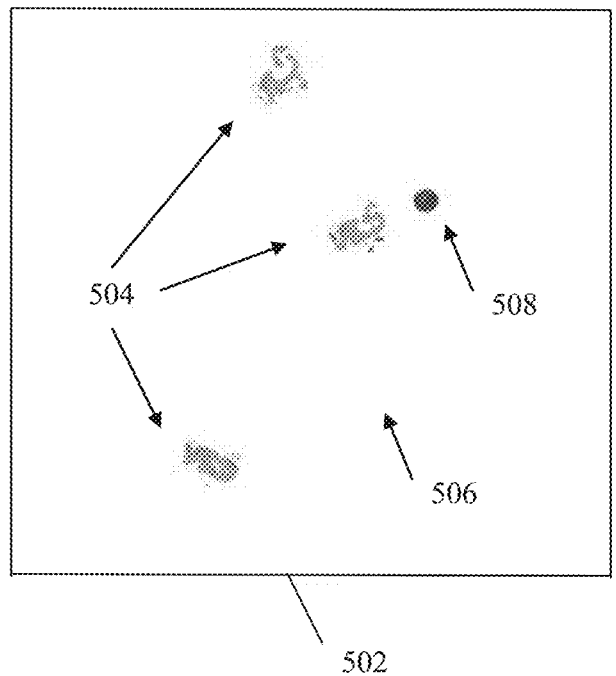
FIG. 5 is a schematic depicting an example of a tissue image for segmentation, in accordance with some embodiments of the present invention.

Reference is now made to FIG. 5, which is a schematic depicting an exemplary of a tissue image 502 for segmentation, in accordance with some embodiments of the present invention.

Tissue image 502 includes cellular tissue objects 504, which are segmented as described herein, for further process. Background 506 of tissue image 502 is excluded from segmentation. A blue pen marking 508, which represents noise, is excluded from segmentation, for example, based on the unique color of the blue pen marking that is not found in tissue.

Referring now back to FIG. 1, at 112, tissue image patches (also referred to herein as patches) are created from the tissue image. It is noted that patches may be created as part of the segmentation process described herein. Alternatively, the patches for segmentation are different than the patches created for further analysis.

Patches may be created according to the design of the image analysis code, for example, at a predefined size and/or predefined resolution according to the size and/or resolution of training images used to train the image analysis code. Patches may overlap, for example, about 10%, or 25%, or 50%, or other values.

The resolution and/or patch size may be selected according to clinical indication, for example, when looking for bacteria, the size of each patch may be relatively small with high resolution, to enable identifying the small bacteria.

At 114, each of the tissue image patches is classified by a patch-level classifier into one or more patch-level tissue types, optionally a single tissue type. Alternatively or additionally, the tissue image patches are segmented by patch-level segmentation code into tissue objects.

As used here, the terms segmentation and detection may sometimes be interchanged, such as when the segmented and/or detected tissue object(s) are indicative of the identified location of the tissue object(s). It is noted that the way in which the tissue object(s) may vary according to segmentation and detection, however, an implementation based on one of segmentation and detection does not exclude an implementation using the other process. For example, segmentation and detection may refer to detecting of cancerous areas of the patch, and/or segmentation of specific types of bacteria within the patch. The term classification refers to assigning a classification category for the patch and/or tissue object(s) as a whole.

The patch-level classifier may be a trained CNN, for example, based on Inception V3. Alternatively, the patches and/or the tissue image as a whole is manually assigned the tissue type(s) by a user, via the GUI. For example, the user may select from a list of medical procedure and/or a list of organs.

The patch-level segmentation code may be implemented as a segmentation CNN (e.g., based on Unet). The patch-level segmentation may output the segmentation as a mask. The patch-level segmentation code may be trained according to patches that are annotated with segmentation markings.

The patch-level segmentation code and the patch-level classifier may be used together, for example, the patch-level segmentation code identifies which pixel elements represent the segmented tissue object(s), and the patch-level classifier classifies the segmented tissue object(s) into the tissue type(s). In another example, the patch-level classifier classifies the patch into the tissue type(s), and the patch-level segmentation code identifies which pixel elements represent the segmented tissue object(s) of the classified tissue type(s).

Optionally, the patch-level classifier outputs, for each respective patch, a vector storing multiple probabilities. Each probability is indicative of the respective patch being classified to one of the possible tissue types which the classifier has been trained to recognize. Alternatively, the patch-level classifier outputs, for each respective patch, a single indication of one of the possible tissue types, for example, the vector is of length 1.

Optionally, each of the classified tissue image patches is associated with a relative location within the tissue image. For example, the patch is associated with metadata indicative the pixel coordinates of the center of the patch within the tissue image. In another example, the patch is associated with coordinates within a two dimensional matrix mapping relative locations of patches.

Optionally, the patch-level classification CNN is trained according to a training dataset of patches from tissue images (i.e., WSIs) from known tissue types of sample individuals. The patches may be manually annotated by a user (e.g., via the GUI) and/or automatically annotated (e.g., according to data extracted from the EMR of the patient indicating the diagnosis and/or procedure performed). The patches may be obtained from segmented patches identified as including tissue objects, as described herein. Patches may be obtained at different resolutions, for example, ×40, ×100, or other values. The patches and associated annotation indicative of tissue type are used to train the CNN to output tissue type(s) for a new inputted patch.

Optionally, the patch-level classification CNN is trained to identify sub-types of tissue.

An example of a tissue type is gastric polyp. An example of sub-types of gastric poly include: normal tissue, hyperplastic tissue, low grade dysplasia, high grade dysplasia, and tubular/tubulovillous.

Another example of tissue type is bacteria. An example of a sub-type of bacteria is *Helicobacter pylori*.

Another example of tissue type is cell. An example of a sub-type of cell is neutrophils.

At 116, the patches are analyzed as a whole tissue image, according to one or more of: the classified tissue type(s), the associated relative location of the respective patch, and the segmentation of the respective patch. The analysis is performed by slide-level analysis code, which may be stored in the memory and executable by hardware processor(s) of the computing device.

For example, for tissue obtained by a stomach biopsy procedure, patches including detected and/or segmented *Helicobacter pylori* bacteria are analyzed with patches including detected and/or segmented types of cells (e.g., neutrophils). The combined data is analyzed to generate a single slide-level tissue type, as described herein.

At 118, one or more slide-level tissue types are computed for the tissue image as a whole according to the analysis of the patches. The slide-level tissue type(s) may be computed according to the patch-level tissue type(s), optionally according to the relative location of the respective patches within the tissue image. The slide-level tissue type may be, for example, an overall diagnosis made for the tissue slide as a whole. For example, malignancy, a benign tumor, a certain disease, or normal tissue. In another example, the slide-level tissue type may be a quantification of various aspects, for example, Ki67 positive nuclei ratio. In yet another example, the slide-level tissue type may be a grade of a calibrated clinical scale, for example, a Gleason grade of a prostate core biopsy, or a grade of a colonic polyp dysplasia. In yet another example, the slide-level tissue type may be indicative of clinically significant features, for example, when cancer cells have penetrated blood vessels of the tissue sample. In yet another example, the slide-level tissue type may be indicative of types of cells present in a biopsy, for example, when the biopsy is from a lymph node, the slide-level tissue type may be indicative of the presence of lymphocytes. In yet another example, the slide-level tissue type may be indicative of the organ and/or position from which the tissue sample was obtained.

It is noted that computing the slide-level tissue type, for example, a final slide-level diagnosis, is more complex than a simple aggregation of the patches. The computation of the slide-level tissue type may be based on cross patch analysis, optionally according to the position of the patches relative to one another. Complexity of computation of the slide-level tissue type arises, for example, due to small errors in the computed patch-level results. When the tissue image is divided into approximately thousands of patches, a very small error percent may lead to some false patch identifications, which when left unchecked may be propagated to errors in the slide-level tissue type. Computation of the slide-level tissue type is designed to account for such patch-level errors, and/or optionally remove such patch-level errors. In another example, the relative location of the analyzed patches affects the slide-level tissue type, for example, in making a final diagnosis. For example, for the case of polyp classification, the tissue of "High Grade Adenoma" and "Malignancy" have the same visual representation in the patch level, and cannot be differentiated at the patch level. The determination whether the slide-level tissue type is "High Grade Adenoma" or "Invasive Carcinoma (Malignant)" depends on whether the identified tissue has invaded beyond muscularis mucosa into submucosa, which requires an analysis of the relative location of the identified patches to reach the final slide-level tissue type.

Exemplary methods for computing the slide-level tissue type(s) are now described. One or a combination of multiple of the following methods may be implemented.

The slide-level tissue type(s) may be computed according to a received indication. The received indication may be obtained, for example, automatically detected by code, manually entered by a user (e.g., selected from a list of indications presented in the GUI), and/or extracted from the electronic medical record of the user. The received indication may include, for example, the organ from which tissue is extracted, fluid sample that includes the extracted tissue, clinical procedure used to extract the tissue, clinical indication performed to obtain the extracted tissue.

The received indication may be computed by detection code that automatically detects the tissue type(s) according to: tissue object(s) of the certain tissue type in the patch(es), patch(es) classified as the certain tissue type, and/or a segmentation of tissue objects of the certain tissue type above a predefined threshold number of pixels of the patch(es) of the tissue image segmented as the certain tissue type. For example, for the received indication of polyp, exemplary potential slide-level type type(s) include: hyperplastic, low grade adenoma, high grade adenoma, and malignant. Optionally, the slide-level tissue type(s) include slide-level sub-tissue type(s), for example, for slide-level tissue type of Adenomatous Lesion, potential sub-tissue type(s) include tubular, tubulovillous, and villous. In another example, for the received type of stomach biopsy, exemplary potential slide-level type type(s) include: gastritis (e.g., type of gastritis such as chronic or acute), amount of *Helicobacter Pylori* bacteria (e.g., none, few, many), and presence of dysplasia. In yet another example, low grade adenoma is computed as the slide-level tissue type when more than a predefined number and/or percent of patches are computed with patch-level tissue type of low grade adenoma, and no patches are computed with patch-level tissue type of a higher diagnosis.

The slide-level tissue type(s) may be computed by one or more classifiers, for example, support vector machine (SVM), and/or CNNs. The SVM may be used, for example, when features are represented as numbers rather than images. The CNN may be used when images, optionally images patches are being analyzed. The classifier receives as input the computed patch-level tissue type(s) and associated location of the patches, for example, the single patch-level tissue type computed for each patch, or a vector of probabilities indicative of probabilities for multiple possible tissue type(s) computed for each patch. In the case of using a CNN for classification, the input to the CNN is an image where each pixel is the output of the corresponding patch in the tissue image. The pixel may store a vector of numbers (e.g., the probability vector of the candidate tissue types that the CNN has been trained on) and/or a single tissue type. When the size of the image is unsuitable for input into the CNN, the image may be resized, using image resizing techniques to a predefined size for input into the CNN. It is noted that the patch-level tissue type(s) may be orthogonal classification that are processed to arrive at one or more slide-level tissue types, for example, a single slide-level diagnosis. For example, for classifying the type of Gastritis in a tissue image of tissue extracted by a stomach biopsy, segmentations of neutrophil cells in patches of the tissue image and/or classification and/or number of Helicobacteri Pylori and/or their detected locations may be provided as input into the classifier.

In some implementations, each classifier (e.g., CNN and/or SVM) is trained to compute a single slide-level tissue type for the tissue image. In other implementations, the classifier is trained to compute one or more slide-level tissue types according to multiple possible slide-level tissue types. The classifier(s) may be selected according to the received indication. The classifier is trained according to a training dataset of training tissue images, each including a respective indication of slide-level tissue type, which may be obtained, for example, manually entered by a user (e.g., via the GUI) and/or extracted from a pathology report and/or from a diagnosis stored in an electronic medical record of the patient. Each tissue image is divided into tissue images patches which are classified into patch-level tissue type(s) as described herein. Each patch is associated with a relative location within the respective training tissue image, for example, a value within a two dimensional array where each cell of the array corresponds a location of one patch relative to the tissue image, a two dimensional index indicating relative position within the tissue image relative to a corner (e.g., [2,4] denotes the patch is the second patch along the x-axis from the left lower corner of the tissue image, and the fourth patch along the y-axis from the left lower corner.

The slide-level tissue type(s) may be computed according to a set of rules. The set of rules may be selected according to the received indication. For example, the set of rules denotes multiple patch-level tissue type(s) that are simultaneously present in the same tissue image, optionally having relative locations to one another. In another example, the set of rules denote a threshold of the number of patch-level tissue type(s) detected for the same tissue image. The slide-level tissue type(s) is computed for when the number is above the threshold. For example, when the patch-level tissue type(s) is a certain type of bacteria, and when a sufficient number of patches include the certain type of bacteria, the slide-level tissue type(s) is computed accordingly. When he number of patch-level tissue type(s) is below the threshold, the tissue type may be "unknown". When the tissue type is "unknown", instructions for obtaining another tissue sample may be generated.

The slide-level tissue type(s) may be computed according to an analysis of an estimated area of tissue objects detected in the patches of the tissue image. The analysis may be according to the set of rules. For example, an estimated number of a certain type of bacteria results in a certain slide-level tissue type.

A probability heatmap. Each pixel of the heatmap corresponds to a certain tissue image patch and includes a value indicative of the patch-level tissue type of the corresponding tissue image patch. For example, pixel (3,5) of the heatmap corresponds to patch (3,5), and pixel (4,2) corresponds to patch (4,2). Pixel (3,5) is assigned value(s) that appear as the color blue on a display, which corresponds to one patch-level tissue type. Pixel (4,2) is assigned value(s) that appear as the color red on the display, which corresponds to another patch-level tissue type. Features, optionally geometrical features, are extracted from the probability heatmap according to multiple feature thresholds and/or ranges. The feature thresholds may be selected according to predefined values corresponding to tissue types. A respective binary mask is computed according to the respective features extracted according to respective feature thresholds. The extracted features may be according to values corresponding to each candidate tissue type, creating a respective binary mask for each tissue type. Additional geometrical features are extracted from each respective binary mask. The slide-level tissue type(s) is computed according to the extracted geometrical features of the respective binary masks. For example, by a trained classifier, optionally a classifier (e.g., CNN and/or SVM) trained according to a training dataset of features extracted from binary masks and ground truth slide-level tissue type(s).

For each pixel element of each patch of the tissue image patches, a respective pixel element level segmentation is computed. The pixel element segmentation includes a probability of the respective pixel element being associated with the patch-level tissue type(s). The number of computed probabilities corresponds to the number of pixels of each patch, such that each pixel of each patch is associated with a respective probability value. Geometrical Features are extracted according to the pixel element level segmentation of each patch. The geometrical features are computed based on relative locations of at least two segmented pixels of at least two patches, for example distance and/or a vector between the two segmented pixels that spans at least two patches. The slide-level tissue type(s) are computed according to the extracted features. For example, by a trained classifier, optionally a classifier (e.g., CNN and/or SVM) trained according to a training dataset of extracted features and ground truth slide-level tissue type(s).

Exemplary features (optionally geometric) extracted from the probability heatmap and/or geometrical features extracted from the binary masks include one or more, or combination of: size of a largest connected area in the mask and/or heatmap, eccentricity of the largest connected area in the mask and/or heatmap, solidity of the largest connected area in the mask and/or heatmap, extent of the largest connected area in the mask and/or heatmap, number of pixels above a pixel threshold, and/or distance between largest connected areas.

A heatmap is computed according to the computed patch-level tissue type(s) and associated location of the patches, for example, the single patch-level tissue type computed for each patch, or a vector of probabilities indicative of probabilities for multiple possible tissue type(s) computed for each patch. The heatmap includes multiple heat pixels, each corresponding to a respective patch. Each heat pixel stores the vector associated with the respective patch, or the single patch-level tissue type computed for the respective patch. Geometrical attributes (also referred to herein as features) of the heatmap image are computed. Exemplary geometric attributes include number of heat pixels in each unique region (e.g., per color of heat pixels), number of unique regions (e.g., clustered according to unique colors), and distance between unique regions (e.g., measured from closest edge to closest edge, from mass centers of the regions). The slide-level tissue type(s) are computed according to the geometrical attributes, for example, by a trained classifier, optionally a CNN and/or support vector machine (SVM) and/or other classifier methods, trained according to a training dataset of geometrical attributes and ground truth slide-level tissue type(s).

At 119, a multi-slide level tissue type(s) is computed for multiple tissue images, and/or for a 3D tissue image. The multiple slides and/or 3D tissue image may be produced, for example, from the same biopsy, and/or same target tissue (e.g., slices of frozen section), and/or from the same sample of body fluid. The slides may be created with the same stain, or from different stain types, where different processes are used to analyzing the tissue images created from different stain types. In such case a slide-level tissue type (e.g., per-slide diagnosis) may be computed as described with reference to act 118. The multi-slide level diagnosis (e.g., biopsy level analysis, frozen section level analysis, body fluid level analysis) may be performed according to the slide-level analysis and/or slide-level tissue type(s), using multiple slides. Alternatively or additionally, the multi-slide level analysis is performed according to the patch-level tissue type(s) (e.g., as described with reference to act 114) and/or analysis of patches (e.g., as described with reference to act 116).

The multi-slide level analysis may be performed according to one or a combination of the following exemplary processes:

The multi-slide level diagnosis may be computed according to a set of rules based on the received indication (e.g., procedure type, biopsied organ). The predefined rules may be based on the results computed for each slide image and/or patches of the slides to compute the multi-slide level type(s) (e.g., overall diagnosis). For example—selecting the highest level of a defined pathology in the biopsy slides (e.g. if one slide image is computed as "Normal" and another slide image is computed as "Malignant", the final diagnosis will be computed as "Malignant"). In another example, decisions are made independently for each tissue image of each slide (e.g., make one decision based on one slide image, and another decision based on another slide image)—for example in an implementation of a certain type of staining that shows a certain type of bacteria, determine on the existence of bacteria based on the slide image with the staining, and decision concerning other pathologies based on different staining.

In implementations where the slides are using the same stain the slides may be concatenated into one large slide. In such implementation the slide-level analysis is performed in the same way only on a larger slide. For example, as described with reference to 110-118 and 120-124.

In another implementation, a classifier (e.g., SVM, CNN) is trained to compute the multi-slide level tissue type(s) (e.g., overall diagnosis) according to an input of the slide-level tissue type(s) and/or patch-level tissue type(s) from patches of multiple slide images. The classifier may be trained according to the process described herein for computing the slide-level tissue type(s) adapted to compute the multi-slide level tissue type(s).

In another implementation, a heat map is computed and analyzed to compute the multi-slide level tissue type(s) (e.g., overall diagnosis). The heat map is may be computed and analyzed according to the process described herein for creating and analyzing the heat map adapted for compute the multi-slide level tissue type(s).

In some implementations the slides may be sequential (e.g., produced from sequential cuts in the original tissue biopsy, for example, consecutive parallel slices). In such an implementation the slides may be registered to one another, for example, by registration code that tracks corresponding pixels and/or regions across the slices. In another example, the sequential slices may be aggregated to generate 3D voxels. After registration and/or aggregation, the multiple slides may be processed as a single slide image with more data and/or bands (e.g., conceptually similar executing multiple analysis processes on the same slide). In such an implementation, after registering and/or aggregating the different slide images, the slide-level analysis is performed as described with reference to act 114 and/or 118, including the additional data extracted from the registered pixels and/or voxels.

There are one or a combination of possible ways the registration may be performed. Exemplary methods for computing the slide registration is now described:

Connected components of the tissue objects in each slide are determined, where each component is labeled. Tissue objects may be identified as described herein.

For each respective slide—registration of the connected component of the respective slide is performed for example using template matching with the connected components of one or more other slides (e.g., immediate nearest neighbors, sequentially before and/or after the slide). For example, the highest match (for example, according to a matching probability score above a predefined threshold) is selected and the registration parameters are saved. Once two connected components match, the matched components are not searched any more in the next iteration of the registration. At the end of the process each connected component in the slide image has its own registration parameters, where some connected components might not have any registration (since one slide image may have more components than the other slide image(s)).

Imaging data (e.g. pixels) of the respective slide are transformed by a transformation function for fitting according to the registration (e.g., registration parameters). Small holes which may be created during the transformation process are filled (for example, using a flood-fill process). Areas where there is no registration (e.g., since one slide image more have more data than other slide images) are removed, or appended to the end of the slide image with imaging data from only one of the slide images. At 120, instructions for treatment of the patient are generated according to the analysis, optionally according to the computed slide-level tissue type(s), and/or according to patch-level tissue type(s), and/or according to the computed multi-level tissue type(s). The instructions may be generated according to a set of rules applied to the analysis, the slide-level tissue type(s) and/or patch-level tissue type(s) and/or multi-level tissue type(s). The instructions may be according to, for example, the clinical procedure being performed, and/or clinical indication. The clinical procedure and/or clinical indication may be manually selected by the user (e.g., from a list presented in the GUI), and/or automatically determined by code (e.g., from an analysis of the tissue image, and/or extracted from the electronic patient medical record).

The set of rules may define an indication of adequacy of the tissue image. Exemplary sets of rules include: blurry tissue image, poor sample preparation, unclean margins, identified tissue does not correspond to target biopsy location, insufficient tissue for proper classification, and no malignancy detected (e.g., in the sentinel lymph node, in the tissue, in the fluid), abnormal patches and/or tissue object(s) to make diagnosis, insufficient cells are present to make a proper diagnosis, and/or when incorrect cells are present which are different than expected cells. When the set of rules is met, meaning the tissue image is adequate, the generate instructions may be to stop any further treatment.

Alternatively, when the set of rules is not met, the generated instructions include instructions for additional treatment of the patient. The additional treatment of the patient includes additional treatment to obtain another tissue sample from the patient. When the additional tissue sample is obtained and another tissue image is created, the acts of the method described with reference to FIG. 1 are iterated for analysis of the another tissue image of the another tissue sample. The analysis of the additional tissue image may be compared to the previous analysis (e.g., to determine whether the same problem remains or whether a new problem arose and/or whether an improvement has been obtained), and/or the analysis may be performed independently for each tissue image.

At 122, the GUI is updated for presentation of the computed slide-level tissue type(s) and/or multi-slide level tissue type(s). The GUI is designed to present tissue images and/or patches of the tissue image and/or the registered slide(s) and/or the 3D tissue image. The GUI presents computed results described herein, for example, segmentation of tissue objects, classification results of tissue type(s) per patch and/or slide-level tissue type(s). The GUI may present a generated report, which may be based on a pathology template. The GUI may include features for easy navigation between the different patches of the tissue image, and/or for navigation of the computed results.

It is noted that alternatively or additionally to presentation within a GUI, other user interfaces may be used and/or updated, for example, audio may be played over speakers, an email may be generated and sent to a client terminal, a video may be generated and played, text may be generated and presented, a pop-up window may be displayed.

The GUI may include a feature for adjusting the computed results and/or approving the computing results.

The GUI may present regions (e.g., patches) of the tissue image for further manual investigation by a user, for example, according to classified and/or detected and/or segmented patches and/or tissues objects, which may be defined according to a set of rules, for example, tissue objects classified as bacteria, and patches with abnormal tissue objects, and patches classified as including malignant cells.

The GUI may include a feature for selection of a patch, for which similar patches are found, as described with reference to act 402 of FIG. 4. Similar patches with similar metadata and/or annotations (e.g., ground truth, diagnosis) may be grouped together. The GUI may include a feature for presenting the entire tissue image associated with one or more of the matched similar patches. The location of the matched similar patch may be marked relative to the whole tissue image, for example, with a rectangle having dashed borders.

The GUI may present the identified abnormal regions and/or tissue object(s) described with reference to act 404 of FIG. 4. The abnormal regions and/or tissue object(s) may be marked within the presented patch and/or within the presented tissue image, for example, with a polygon having dashed borders.

The GUI may be designed to provide the user (e.g., pathologist, surgeon, radiologist) with control of the final results (e.g., diagnosis), where at least some of the systems, methods, apparatus, and/or code instructions described herein provide automated assistance to improve the work of the pathologist, to be more accurate and/or more efficient, and/or improve the user of the user performing the medical procedure by providing real time instructions (e.g., to make sure adequate tissue samples are obtained), as described herein. The GUI may be presented on a display, for example, located within the procedure room (e.g., clinic, operating room) such as for real time guiding of the procedure (e.g., biopsy), and/or in the pathology lab such as for automated assistance in analyzing tissue samples.

The instructions for further treatment of the patient, or to avoid further treatment, may be presented within the GUI. For example, as a text message, played as an audio file, and/or a video may be shown instructing the user on what to do in the next treatment to obtain a proper tissue sample (e.g., proper FNA practices). The GUI may be dynamically updated in response to additional tissue images of additional tissue samples obtained according to previous instructions. Exemplary instructions include: obtain another tissue sample from same location, obtain another tissue sample from another location, obtain another tissue sample at a defined location, and unclean surgical margins—excise additional tissue.

Optionally, a report is generated. The report may be presented within the GUI. The report may be based on a template of pathology reports. The report may be viewed by the user (e.g., pathologist) and optionally approved. The approved report may be provided to the physician that ordered the study and/or stored in the EMR of the patient.

Alternatively or additionally, a video is played showing different regions (e.g., patches) of the tissue image used to determine the slide-level tissue type.

Figure 6:
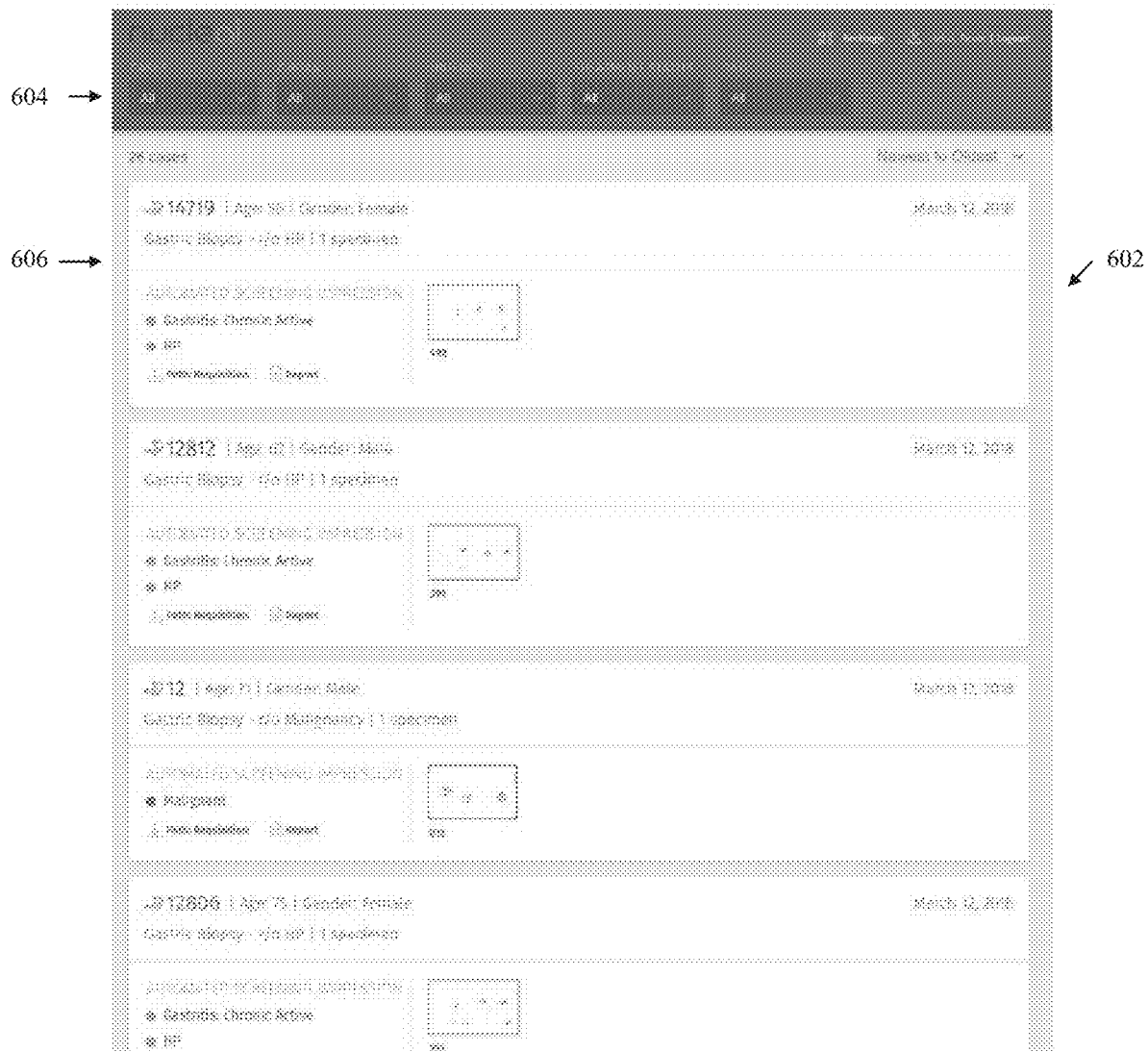
FIG. 6 is a schematic of an exemplary GUI presenting a list of automatically analyzed tissue images, in accordance with some embodiments of the present invention.

Reference is now made to FIG. 6, which is a schematic of an exemplary GUI 602 presenting a list of automatically analyzed tissue images, in accordance with some embodiments of the present invention. Cases may be sorted and/or filtered according to a menu 604, for example, per specific case, according to organ from where the tissue was obtained, according to urgency of the procedure, according to treatment status, and/or according to date. Window 606 presents an example of a case, including, for example, patient demographic data, procedure performed (e.g., gastric biopsy to rule out HP), and results of the automated analysis (e.g., Gastritis: Chronic Active, and HP). The user may select a certain case to obtain additional details, for example, view the tissue image, view the patches, view the automated report, and/or other computed results.

Figure 7:
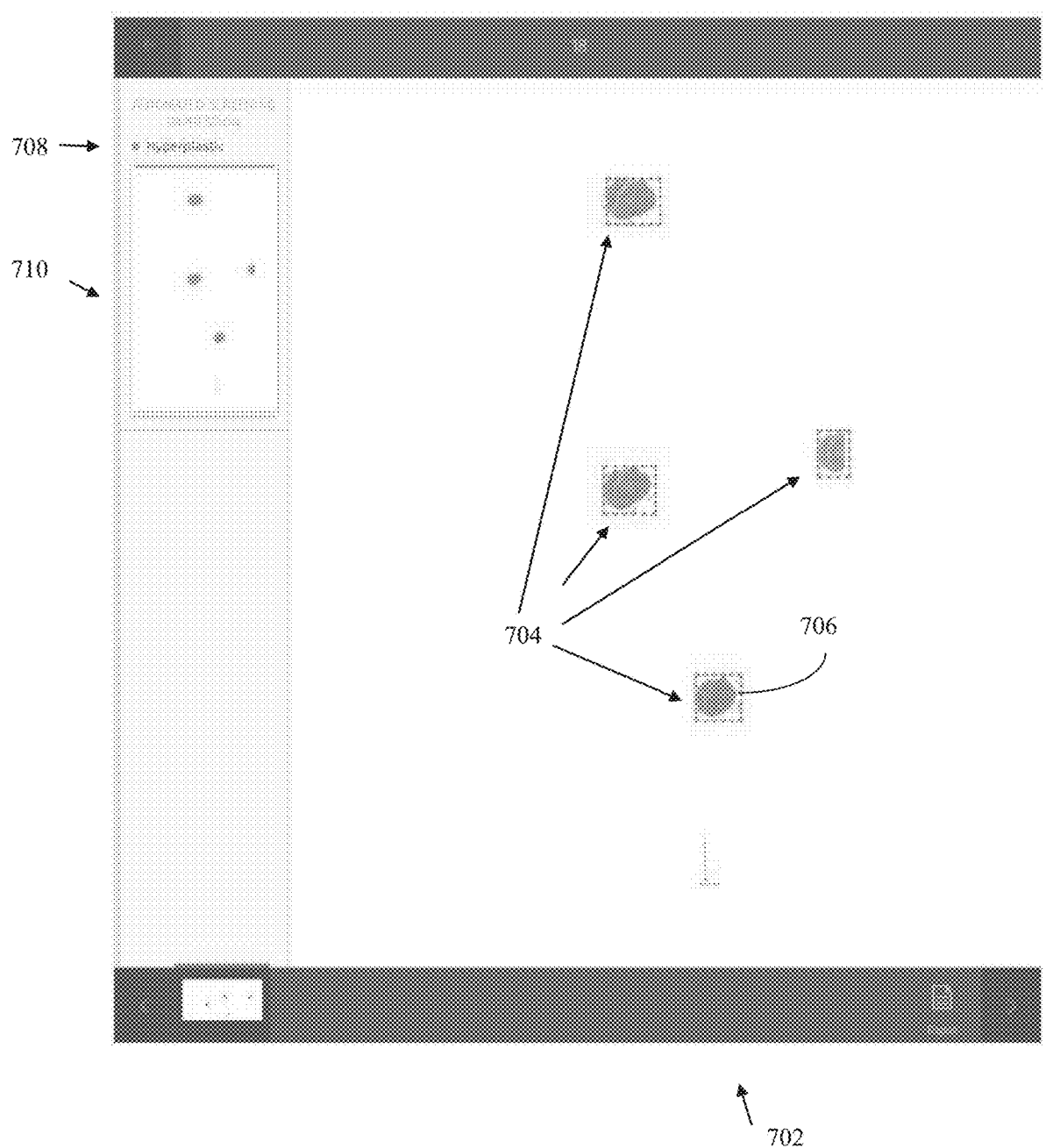
FIG. 7 is a schematic of an exemplary GUI presenting the tissue image created from a certain physical slide with tissue sample extracted from the patient, in accordance with some embodiments of the present invention.

Reference is now made to FIG. 7, which is a schematic of an exemplary GUI 702 presenting the tissue image created from a certain physical slide with tissue sample extracted from the patient, in accordance with some embodiments of the present invention. GUI may present automatically segmented, classified, and/or identified tissue objects 704, for example cells. The automatically segmented, classified, and/or identified tissue objects 704 may be delineated by borders (e.g., one border 706 marked for clarity of explanation), for example, a rectangle of dashed lines. GUI 702 may further present the computed slide-level tissue type 708 (e.g., hyperplasia), and/or may present a thumbnail 710 of the whole tissue image and/or of the patch.

Figure 8:
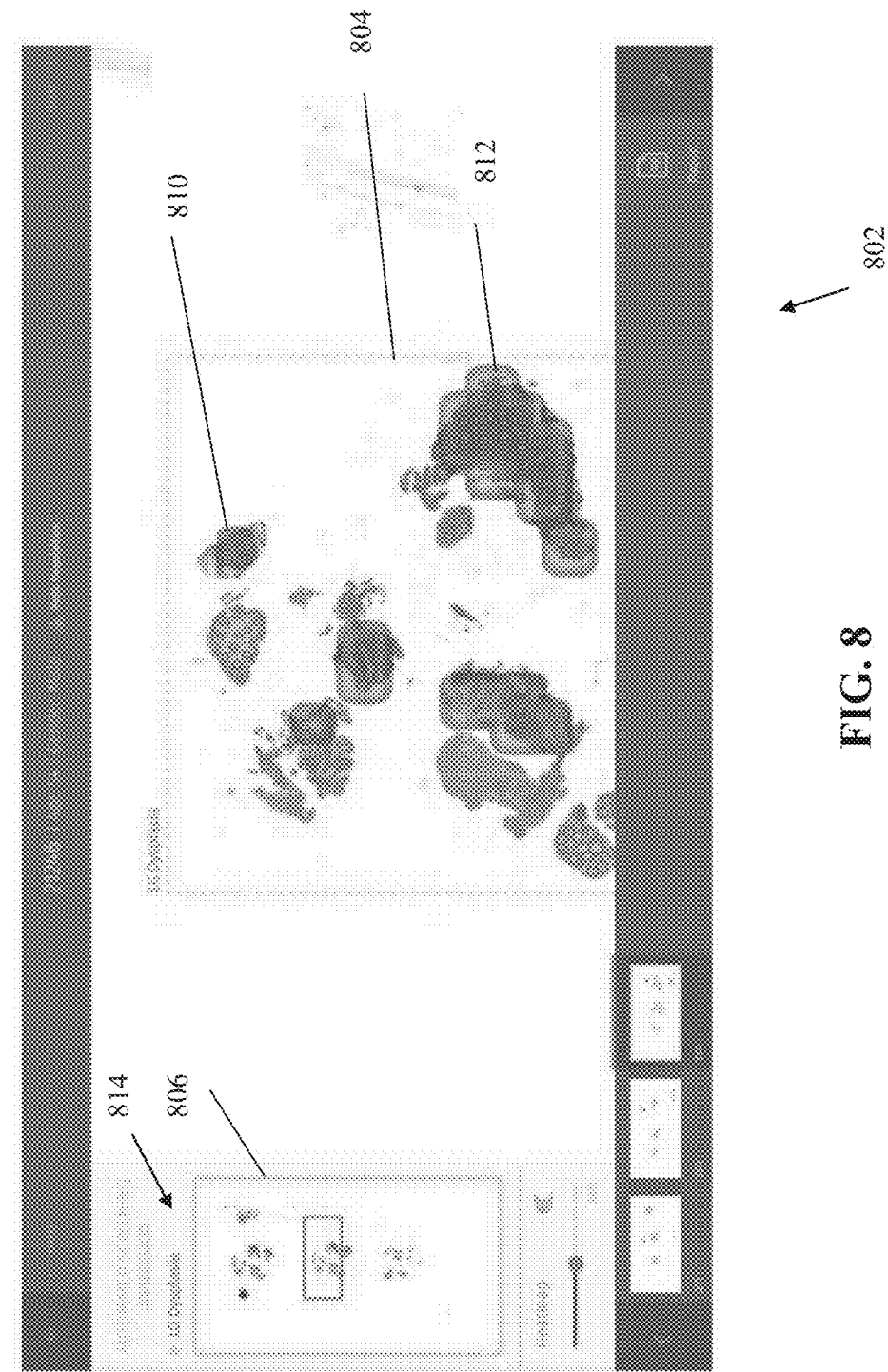
FIG. 8 is a schematic of an exemplary GUI presenting a computed heatmap overlaid on a tissue image and/or patch of the tissue image, in accordance with some embodiments of the present invention.

Reference is now made to FIG. 8, which is a schematic of an exemplary GUI 802 presenting a computed heatmap overlaid on a tissue image and/or patch of the tissue image, in accordance with some embodiments of the present invention. As shown, patch 804 is a zoom in of tissue image 806. For clarity of explanation, portions 810 and 812 of heatmap are marked, where for example, 810 is shown in one color (e.g., blue) and 812 is shown in a different color (e.g., red). For example, blue regions marked by 810 may be indicative of a certain probability range (e.g., 0-50%), or may be indicative of a certain patch-level tissue type computed for the corresponding patch(es). Red regions marked by 812 may be indicative of another probability range (e.g, 51-100%), or may be indicative of another patch-level tissue type computed for the corresponding patch(es). GUI 802 may present the computed slide-level tissue type(s) 814 (e.g., LG Dysplasia).

Figure 9:
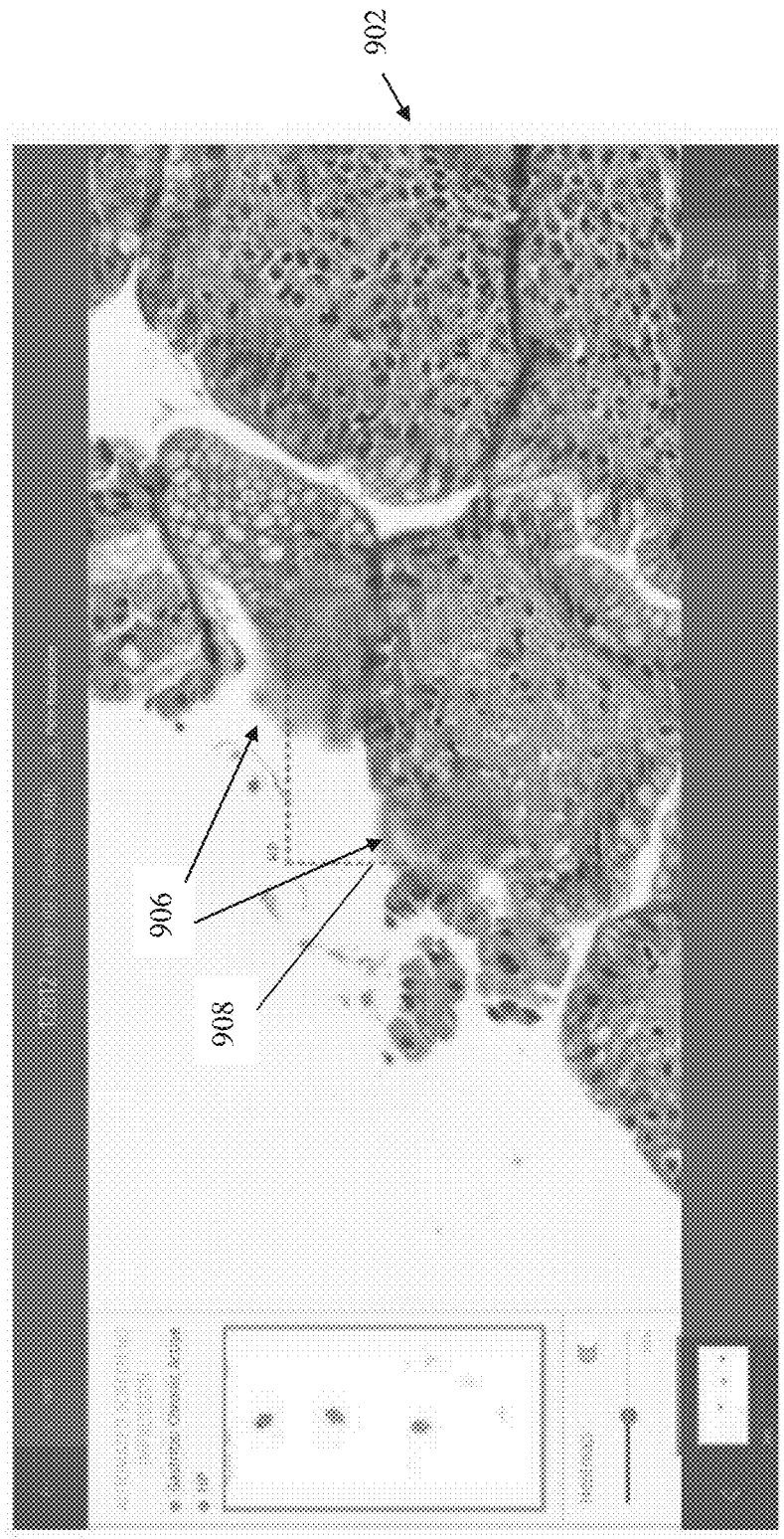
FIG. 9 is a schematic of an exemplary GUI presenting a computed segmentation shown in association with a heatmap, along with detection results, in accordance with some embodiments of the present invention.

Reference is now made to FIG. 9, which is a schematic of an exemplary GUI 902 presenting a computed segmentation shown in association with a heatmap 906, along with detection results 908, in accordance with some embodiments of the present invention. The region covered by heatmap 906 may denote the segmentation of the tissue objects, *Helicobacter Pylori* bacteria in the present case. Colors of heatmap 906 may be indicative of, for example, the probability of each pixel denoting the *Helicobacter Pylori* bacteria, for example, red denoting relatively high probability and blue denoting relatively lower probability. Detection results 908 may indicate the detected location of *Helicobacter Pylori* bacteria, for example, shown as a square with dashed lines. Detection results 908 may be computed, for example, per patch. Detection results 908 may be computed by detection code, and/or the classifier code.

Figure 10:
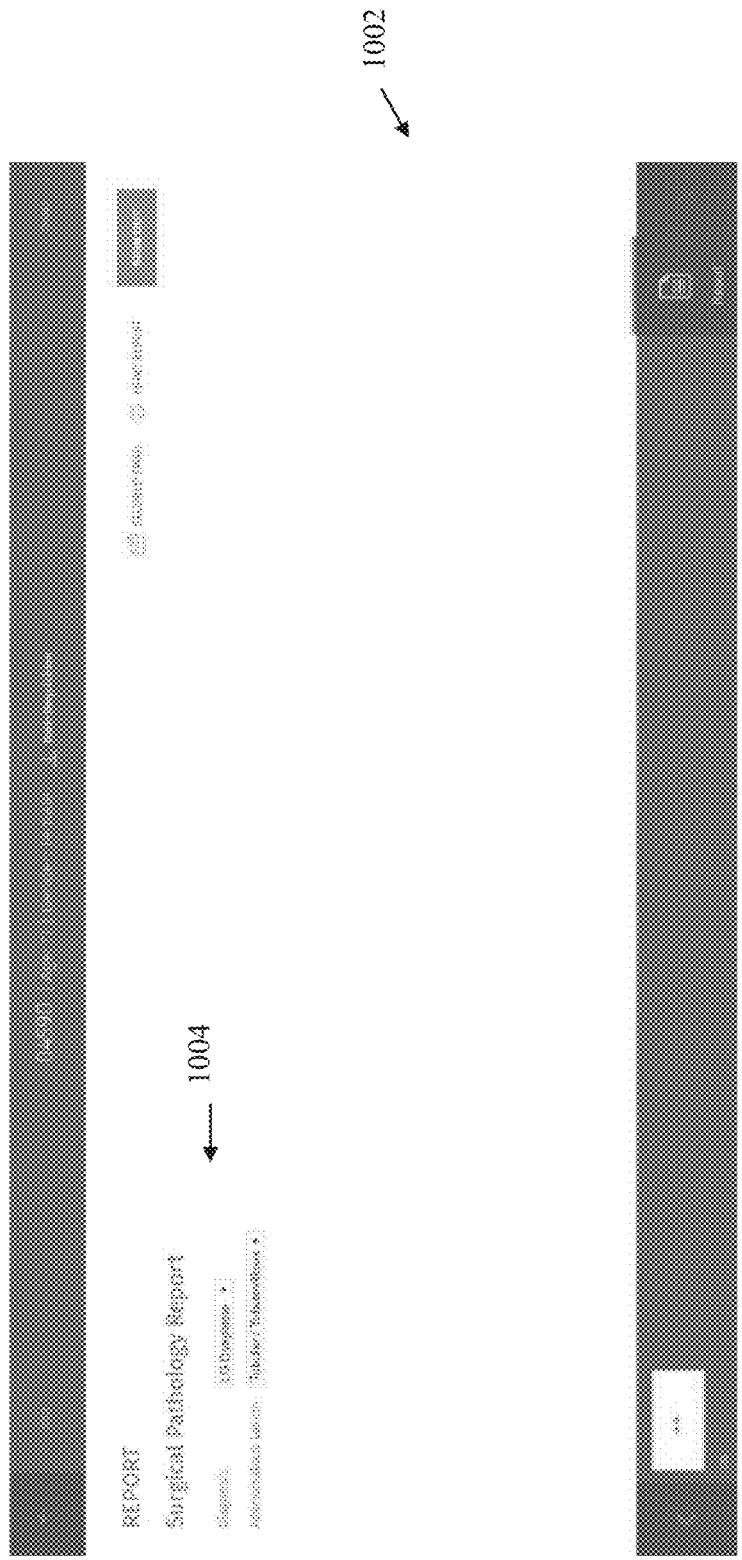
FIG. 10 is a schematic of an exemplary GUI presenting the computed results for automatically generating the pathology report, in accordance with some embodiments of the present invention.

Reference is now made to FIG. 10, which is a schematic of an exemplary GUI 1002 presenting the computed results 1004 for automatically generating the pathology report, in accordance with some embodiments of the present invention. Results 1004 may include, for example, the slide-level tissue type (e.g., diagnosis), and/or patch-level tissue type (e.g., of the detected tissue object(s)). Results 1004 may be adjusted by the user, and/or approved for automatically generating the report.

At 124, one or more acts 102-122 are iterated, for dynamically updating the GUI. For example, another tissue sample is obtained when the current tissue sample is inadequate, another tissue image may be created and analyzed, as described herein. The GUI is updated according to the new tissue image.

Referring now back to FIG. 3, at 302, training tissue images are obtained for multiple sample individuals. The training tissue images may be of different tissue types, for example, obtained by different procedures, of different organs, of different body fluids, and/or obtained for different clinical indications.

At 304, the tissues images are annotated. The annotation may be obtained from pre-stored data, for example, a pathology report, a diagnosis code, and/or other data stored in the patient medical record. The annotation may be manually performed by a user. Each tissue image is annotated at the slide-level with a slide-level tissue type, and/or at the pixel element level. The pixel element level annotation may be, for example, a segmentation of tissue object(s) with an associated tissue type assigned to the segmented region.

At 306, one or more patches and/or tissue images segmented at the pixel element level are created by a user via the GUI. The user may start from an unannotated patch of a tissue image, where the tissue image is unannotated, or annotated at the slide-level. The user delineates one or more pixel elements indicative of a tissue object denoting a certain tissue type, for example, by manually marking a border around the tissue object. The border may be marked using the GUI, for example, a freeform line drawn around the tissue object, a polygon drawn around the tissue object, and/or a rectangle drawn to include the tissue object therein. The user may select individual pixel elements, and/or groups of pixel elements by marking the border around the group of pixel elements (e.g., polygon, rectangle). For example, the user selects each bacteria in the image and/or patch, and/or selects nuclei of a certain type. The user may manually enter the tissue type to associate with the selected pixel element. The tissue object is segmented by segmentation code, for example, all pixel elements within the defined region are segmented. Pixel elements of the segmented tissue object are designated as indicative of the certain tissue type. The patch with annotated segmented tissue object is stored in the sub-set of training images having pixel element level annotation.

At 308, the training images may be arranged into one or more training datasets for training classifiers and/or segmentation code for computing patch-level tissue type(s). Training dataset may be organized, for example, according to tissue types, according to procedure type, according to target organs from which the tissue sample was extracted, according to body fluid, and/or according to clinical indications.

At 310, a pixel element level classifier, optionally implemented as a CNN, is trained. The pixel element level classifier is trained according to the sub-set of training images that include pixel element level annotation.

The pixel element classifier may be used as the segmentation code and/or detection code described herein (e.g., with reference to the process of FIG. 1 and/or FIG. 4), for segmentation and/or detection of tissue object(s) in patches.

At 312, the pixel element level CNN is further trained according to patches created from each training image of another sub-set of training images that include slide-level annotation. The other sub-set of training images do not include pixel level annotations. Optionally, patches of the training images that include slide-level annotations are selected for the training. Patches may be selected manually by a user, and/or may be automatically selected, for example, all patches are selected, or patches with pixels indicative of objects other than background are selected (i.e., patches with only background are excluded).

The pixel element level CNN is trained according to a loss function based on distance to a certain patch of the patches of each training image that includes slide-level annotation, associated with highest probability of belonging to the slide-level tissue type of the tissue image from which the certain patch is extracted.

Optionally, the initial probabilities of belonging to the slide-level tissue type(s) of the tissue image associated with the certain patch are computed by the trained pixel element level CNN. The initial probabilities are adjusted according to the loss function.

Alternatively, when the training images include tissue images with only slide-level annotations, the classifier and/or segmentation code may be trained based on multiple instance learning (MIL) approaches. MIL training approaches are based on diving the slide-level annotated tissue image into multiple patches (referred to as bags), where a model is trained for all patches. The loss function of the model during training is based on the slide-level annotation, according to the distance to the patch with the highest probability of belonging to the category of the slide-level annotation.

Alternatively to acts 310 and 312, the CNN is trained, optionally simultaneously and/or during the same training round(s), using both training images with pixel-level annotation and training images with slide-level annotation. The ground truth used for training the CNN is indicated according to a location of a respective patch of the sub-set of training images including the pixel element level tissue type(s), and according to the sub-set of images with slide-level tissue type annotation, wherein only patches with highest probability above a threshold indicative as belonging to the slide-level tissue type according to the CNN are considered for training the CNN.

At 314, the trained pixel element classifier code is provided, for example, stored in memory and/or the data storage device of the computing device. The pixel element classifier may be stored as the segmentation code and/or detection code described herein (e.g., with reference to the process of FIG. 1 and/or FIG. 4), for segmentation and/or detection of tissue object(s) in patches.

Referring now back to FIG. 4, act 402 relates to identifying one or more tissue image patches that are similar to a selected patch of the tissue image. The similar tissue image patches are obtained from a dataset storing tissue images acquired for other sample individuals. Act 402 may be executed, for example, after and/or simultaneously with one or more acts 112-124 of FIG. 1. Act 404 relates to detecting abnormal patches in the tissue image. Act 404 may be executed, for example, after and/or simultaneously with one or more acts 112-124 of FIG. 1. Act 406 relates to comparing the computed slide-level tissue type(s) with a manual diagnosis. Act 406 may be executed, for example, after and/or simultaneously with one or more acts 118-124 of FIG. 1.

At 402, another patch from another tissue image of another patient that is similar to one of the patches of the tissue image of the patient is identified. The similar patch may be identified, for example, for training purposes (e.g., showing other similar cases to students learning to analyze histology slides), and/or for diagnosis purposes (e.g., in a difficult case, presenting results of previously similar patches to aid the user in determining the diagnosis for the current case)

An exemplary process for identifying similar patches is now described. A patch is selected from the tissue image, optionally via the GUI, for example, the user may click on one of the patches computed from the tissue image and/or click on a certain pixel element where the patch associated with the pixel element is selected, and/or may create their own patch by marking an outline on the tissue image (e.g., a mark a polygon). An encoding (which may sometimes be substituted with the term embedding) is computed for the selected patch by a trained autoencoder code, optionally an autoencoder CNN. The encoding may be stored as a feature vector. One or more similar patches are identified from a dataset of patch encodings, according to a requirement of a similarity distance between the encoding of the selected patch and encoding of the patches in the dataset. The similarity distance may be computed, for example, by considering each encoding as a point in a multidimensional space and computing the distance between the points in the multidimensional space, a correlation function that computes a correlation value, and/or other methods. The threshold may be defined by the user, set as a predefined value, and/or computed by code. The threshold may be dynamically adjusted. A set of one or more (e.g., multiple) similar patches is identified. Optionally, one or more matching patches are identified from the similar patches according to a match between the computed tissue type(s) of the selected patch and tissue type(s) of the similar patches. Alternatively, the dataset is filtered in advance of the distance of the computation, such that the distance is computed for patches of the dataset matching the tissue type(s) of the selected patch.

The matching similar patch(es) may be presented in the GUI. Optionally, the identified patch(es) are presented in association with previously analyzed results, for example, tissue types seen in the patch(es), overall diagnosis for the tissue image from which the slide was taken, procedure used to obtain the patch, and data of the patient from which the tissue for the patch was extracted. The similar patch(es) may be presented alongside the current patch. When several matching similar patches are found matching the same tissue type (e.g., hyperplasia polyp), the matches may be grouped together for presentation in the GUI. A similarity score indicative of similarity between the matching patches and the selected patch may be computed and presented. The similarity score may be computed according to the similarity distance.

The autoencoder CNN may be trained according to different tissue images of different tissue types obtained for different sample patients. The patches are labeled with a ground-truth indicative of tissue type(s). The annotation of tissue type may be performed manually by the user, extracted from the EMR (e.g., pathology report), and/or computed as described herein. The autoencoder CNN is trained on patches of each tissue image (i.e., WSI), optionally after tissue objects are segmented. The loss function for training the autoencoder CNN may denote a reconstruction error between the original respective patch of the tissue mage and the corresponding decoded patch.

The dataset of patch encodings stores the encoding of each patch computed by the autoencoder CNN, optionally as a feature vector. The dataset may store the image of the patch and/or metadata associated with the patch (e.g., ground-truth tissue type(s), data of the slide, location of the patch within the tissue image) in association with the encoding of the patch.

At 404, abnormal patches are detected. Alternatively or additionally, abnormal tissue objects within patches are detected. Such abnormal patches and/or tissue objects are indicative of tissue regions where the tissue type(s) cannot be computed, and/or where the probability indicative of the computed tissue type(s) is below a threshold. For example, a diagnosis cannot be made due to the abnormal patches. Such abnormal areas may be flagged for manual inspection by a specialist. The specialist may spend more time inspecting the abnormal areas, which overall saves time in analyzing the tissue image.

A first exemplary process for detecting abnormal patches and/or abnormal visual object(s) in patches is now described. The process is based on determining that the patch and/or tissue object is abnormal according to a statistical distance to the dataset of encoded patches indicative of abnormality. The dataset of encoded patches is described with reference to act 402.

The autoencoder CNN computes an encoding for each patch of the tissue image, optionally after tissue segmentation is performed as described herein. The autoencoder CNN is trained according to patches identified as not abnormal, and/or normal, for example, as described with reference to act 402. It is noted that what is considered normal may vary according to clinical context. The clinical context may be stored in association with the normal patches, for example, as metadata. The patches may be clustered by clusterization code. The cluster centroids may be stored in the dataset. A statistical distance is computed between each encoding of each patch of the tissue image and the patch encodings stored in the dataset. The statistical distance is computed between the encoding of each patch of the tissue image and the cluster centroids and/or the encoded patches stored in the dataset. One or more patches are identified as abnormal when the statistical distance between the respective patch and one or more nearest encoding of patches denoting normal tissue is above an abnormality threshold.

The abnormality threshold may be computed by computing a similarity distance function between encodings of patches determined to be normal (e.g., manually by a user) and the most similar normal encoded patch(es) stored in the dataset (e.g., most similar patches may be found as described with reference to act 402), for example, the sum of the closest distances, the median of the closest distances, the average of the closest distances. An abnormality distance is computed between encodings of patches determined to be abnormal (e.g., manually by a user) and the most similar normal encoded patch(es) stored in the dataset. The abnormality threshold is determined as to how close the normal patches are to other normal patches in the dataset (and/or to cluster centers of normal patches), and still be considered normal. The abnormality threshold may be set such that a certain percentage (optionally all, or about 90%, or about 95%) of normal patches have distances below the abnormality threshold, and a certain percentage (optionally all, or about 90%, or about 95%) of abnormal patches are above the abnormality threshold. The actual value of the abnormality threshold may be computed according to the values of the computed distances. The abnormality threshold may be set according to a desired tradeoff between specificity and sensitivity, for example, according to clinical case.

The abnormality threshold may be set, for example, manual by the user, obtained from a stored predefined value such as according to clinical indication, and/or automatically computed. The abnormality threshold may be dynamically adjusted.

A second exemplary process for detecting abnormal patches and/or abnormal visual object(s) in patches is now described. The process is based on determining that the patch and/or tissue object is abnormal according to a comparison to other patches and/or tissue objects of the tissue image. The patches of the tissue image are clustered. Optionally, each patch is passed through the autoencoder CNN and the encodings are clustered, for example, by clusterization code. The autoencoder CNN is either pre-trained using normal patches, or based on the patches in the current slide training is performed. A distance is computed between each patch encoding and one or more of the cluster centers. Optionally the distance is between the patch encoding and the center of the cluster associated with the patch. One or more patches are identified as abnormal when the statistical distance between the encoding of the respective patch and the cluster center is above an abnormality threshold. Alternatively of additionally, patches located a certain distance away from the center(s) of the cluster(s) are determined to be abnormal. For example, the furthest predefined percentage of patches (e.g., 1-5%, or other values) are determined to be abnormal. Alternatively or additionally, one or more clusters located furthest away (e.g., and/or above an abnormality threshold) from the other clusters (e.g., according to cluster centers) are identified as being abnormal. The patches of the abnormal cluster(s) are identified as being abnormal. Alternatively or additionally, patches located furthest away (e.g., and/or above an abnormality threshold) from other patches are identified as being abnormal.

A third exemplary process for detecting abnormal patches and/or abnormal visual object(s) in patches is now described. The third exemplary process is based on classification consistency by a trained classifier that is dynamically adjusted during each classification iteration of the same patch. Each patch of the tissue image is inputted into a trained patch classifier, optionally a CNN. The patch classifier computes a probability of likelihood of tissue type(s) for the patch. The patch classifier is trained according to patches labeled with tissue type, which may include normal tissue type and/or abnormal tissue types. The same patch is iteratively inputted into the trained patch classifier multiple times, where each time the patch classifier is adjusted, optionally randomly, for example, one or more neurons are dropped (e.g., ignored, excluded) from the CNN. The computed probability of tissue type(s) of the multiple iterations are analyzed. An indication of likelihood of abnormality is computed for the patch when the analysis of the probabilities of tissues types varies according to a consistency requirement.

At 406, the computed slide-level tissue type(s) is automatically compared to a manual diagnosis of the slide. An alert is generated when a mismatch is detected, for example, presented in the GUI, sent as an email, stored as an event for future viewing, sent as a message to a mobile device, and/or a pop-up window on an administrative server. The manual diagnosis may be obtained, for example, from metadata associated with the tissue image, from a pathology report, from the electronic medical record of the patient, and/or manually entered. The manual diagnosis may be made by a user (e.g., pathologist) based on standard methods. The manual diagnosis may be stored, for example, as free text, and/or a predefined diagnostic code.

Figure 11:
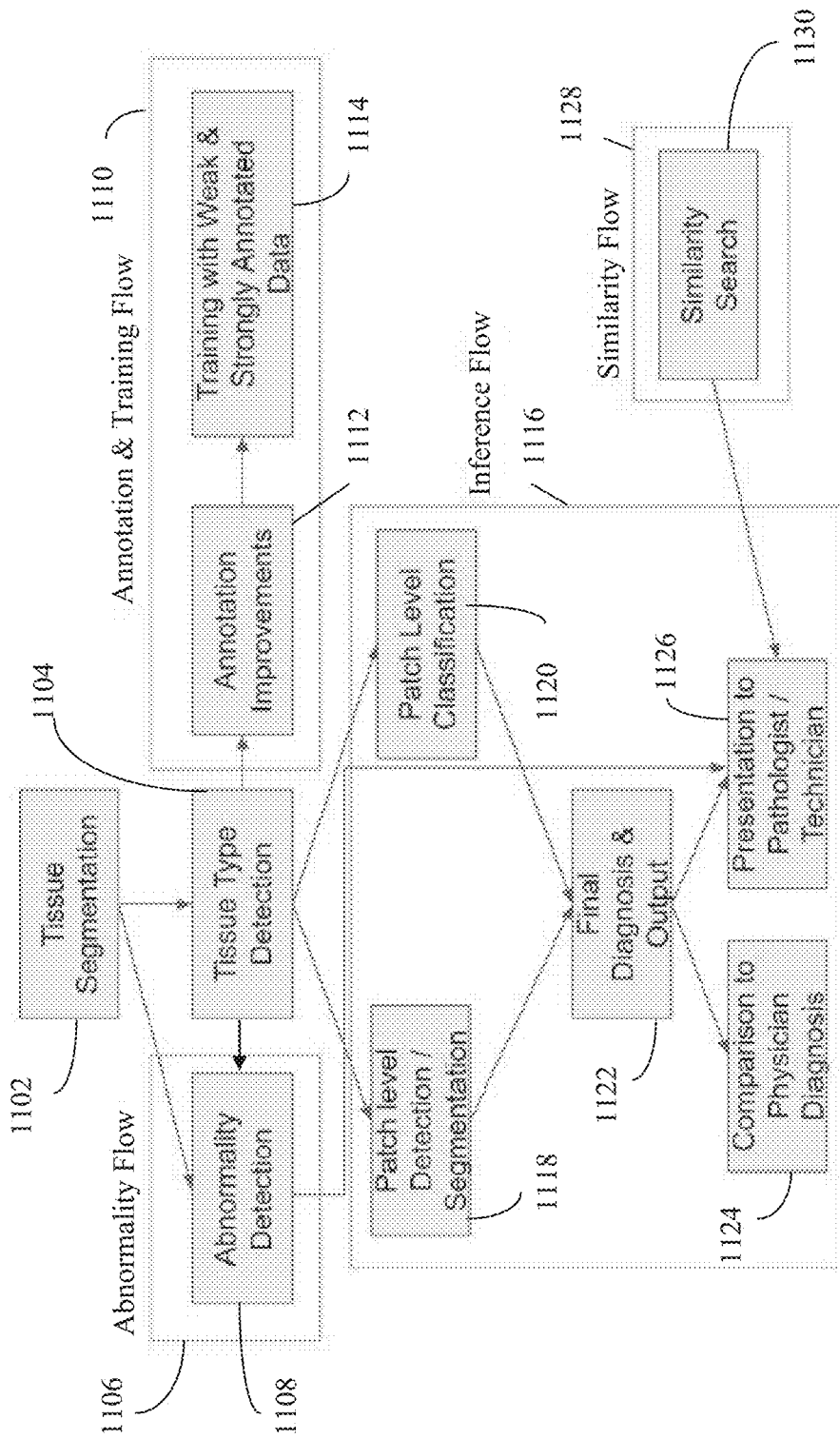
FIG. 11 is an exemplary flowchart of possible dataflow implementations based on the methods described with reference to FIGS. 1,3,4, and/or executable by components of system described with reference to FIG. 2, in accordance with some embodiments of the present invention.

Reference is now made to FIG. 11, which is an exemplary flowchart of possible dataflow implementations based on the methods described with reference to FIGS. 1,3,4, and/or executable by components of system 200 described with reference to FIG. 2, in accordance with some embodiments of the present invention.

Most of the described flows start with tissue segmentation 1102 to exclude background and/or noise (e.g., as described with reference to act 110 of FIG. 1), followed by a tissue type detection feature 1104 to identify the overall tissue being analyzed (e.g., as described with reference to act 114, and/or 118 of FIG. 1).

Abnormality flow 1106 includes an abnormality detection feature 1108 for detecting abnormal tissue object(s) in the segmented tissue, for example, as described with reference to act 404 of FIG. 4.

Annotation and Training Flow 1110 includes an annotation feature 1112 for manual annotation of tissue objects, and/or a feature 1114 for training analysis code such as a classifier, segmentation code, and/or detection code, with weak (i.e., slide-level) and strongly (i.e., per pixel element level) annotated data. Annotation feature 1112 is described, for example, with reference to act 304 of FIG. 3. Training feature 1114 is described, for example, with reference to acts 306-312 of FIG. 3.

Interference flow 1116 is for inferring the image type to compute the slide-level tissue type(s), for example, overall diagnosis. Inference flow 1116 includes a feature 1118 for patch level detection and/or segmentation (e.g., as described with reference to act 110,112, and/or 114 of FIG. 1), a feature 1120 for patch level classification (e.g., as described with reference to act 114 of FIG. 1), a feature 1122 for computational of the slide-level tissue type(s) such as diagnosis (e.g., as described with reference to act 118 of FIG. 1), a feature 1124 for comparison of the slide-level tissue type(s) (e.g., diagnosis) to a manual physician diagnosis (e.g., as described with reference to act 406 of FIG. 4), and a feature 1126 for presenting the results in the GUI (e.g., as described with reference to act 122 of FIG. 1).

Similarity flow 1128 includes a feature 1130 for searching for patches that are similar to a selected path, as described for example, with reference to act 402 of FIG. 4.

Abnormality flow 1106, annotation and training flow 1110, interference flow 1116, and similarity flow 1128 process patches extracted from the tissue image, described, for example, with reference to act 112 of FIG. 1.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is expected that during the life of a patent maturing from this application many relevant tissue images will be developed and the scope of the term tissue image is intended to include all such new technologies a priori.

As used herein the term "about" refers to (10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween. It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the Applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A computer implemented method of computing at least one slide-level tissue type for a tissue image of tissue extracted from a patient, comprising:
    receiving a tissue image of a slide including tissue extracted from the patient;
    segmenting tissue objects of the tissue image;
    creating a plurality of tissue image patches from the segmented tissue objects of the tissue image;
    classifying, by a patch-level classifier, each of the plurality of tissue image patches into at least one patch-level tissue type, wherein each of the classified tissue image patches is associated with a relative location within the tissue image;
    analyzing, by a slide-level analysis code, the classified at least one patch-level tissue type and associated relative location for each of the plurality of tissue image patches outputted by the patch-level classifier, for computing at least one slide-level tissue type for the tissue image; and
    providing the at least one slide-level tissue type.

2. The method according to claim 1, wherein the at least one slide-level tissue type is distinct from the at least one patch-level tissue type.

3. The method according to claim 1, wherein the at least one slide-level tissue type is computed based on two or more distinct patch level tissue types computed for two or more patches.

4. The method according to claim 1, wherein the at least one slide-level tissue type is computed according to at least one geometric feature based on associated relative location of each of the plurality of tissue patches.

5. The method according to claim 4, wherein the at least one geometric feature is selected from the group consisting of: distance between patches, total area of patches of a same patch-level tissue type, area of patches of a same patch-level tissue type directly neighboring one another, patches of a first patch level-tissue type separated by at least one patch of a second patch level-tissue type, density of tissue objects identified in at least one patch, relative angle between patches according to a center point, and combinations of the aforementioned.

6. The method according to claim 1, wherein the associated relative location is according to location of patches of the extracted tissue located on the slide, and excludes relative in-situ anatomical locations within the body of the patient.

7. The method according to claim 1, further comprising: generating instructions for treatment of the patient according to a set of rules applied to the analysis.

8. The method according to claim 7, wherein the instructions for treatment of the patient comprise instructions to obtain another tissue sample from the patient, and further comprising iterating the acts of the method for analysis of the another tissue for generating updated instructions for treatment of the patient.

9. The method according to claim 8, wherein the instructions for treatment of the patient are presented in a graphical user interface (GUI), and wherein the GUI is updated according to updated instructions.

10. The method according to claim 7, wherein the set of rules is indicative of adequacy of the tissue image.

11. The method according to claim 7, wherein when the set of rules is not met the generated instructions include instructions for additional treatment of the patient.

12. The method according to claim 7, wherein the set of rules for generating instructions to obtain another tissue sample include: blurry tissue image, poor sample preparation, unclean margins and instructions to cut additional tissue, identified tissue does not correspond to target biopsy location, insufficient tissue for proper classification, and no malignancy detected.

13. The method according to claim 7, wherein when the set of rules is met the instructions include instructions to stop the treatment.

14. The method of claim 1, wherein the slide-level analysis code comprises at least one CNN trained according to a training dataset comprising a plurality of training tissue images each including a respective indication of slide-level tissue type, a plurality of tissue images patches each classified into at least one tissue type and associated with a relative location of the respective tissue image patch within the respective training tissue image.

15. The method of claim 1, wherein the slide-level analysis code comprises a set of rules selected according to a received indication.

16. The method according to claim 15, wherein the received indication is selected from the group consisting of: organ from which tissue is extracted, fluid sample that includes the extracted tissue, clinical procedure used to extract the tissue, clinical indication performed to obtain the extracted tissue.

17. The method of claim 1, wherein the slide-level analysis code comprises:
    computing a probability heatmap, wherein each pixel of the heatmap corresponds to a certain patch of plurality of tissue image patches and includes a respective value indicative of the patch-level tissue type of the corresponding tissue image patch selected from the group consisting of: a vector storing plurality of probabilities each probability indicative of the respective patch being classified to one of a plurality of possible patch-level tissue types, and a single indication of one of a plurality of possible patch-level issue types associated with each patch;
    extracting features from the probability heatmap according to a plurality of feature thresholds;
    computing a respective binary mask of a plurality of binary masks, according to features extracted according to each feature threshold of the plurality of feature thresholds;
    extracting geometrical features from each respective binary mask of the plurality of binary masks; and
    computing the at least one slide-level tissue type according to the extracted geometrical features of each respective binary mask.

18. The method according to claim 17, wherein features extracted from the probability heatmap and geometrical features extracted from binary masks are selected from the group consisting of: size of a largest connected area in the mask and/or heatmap, eccentricity of the largest connected area in the mask and/or heatmap, solidity of the largest connected area in the mask and/or heatmap, extent of the largest connected area in the mask and/or heatmap, number of pixels above a pixel threshold, distance between largest connected areas, and combinations of the aforementioned.

19. The method according to claim 17, wherein the plurality of feature thresholds are selected according to values of heat pixels corresponding to respective patch-level tissue types.

20. The method according to claim 1, wherein the slide-level analysis code comprises:
- computing, for each pixel element of each patch of the plurality of tissue image patches, a pixel element level segmentation including a probability of the respective pixel element being associated with the at least one patch-level tissue type;
- extracting geometrical features according to the pixel element level segmentation of each patch, wherein the geometrical features are computed based on relative locations of at least two segmented pixels of at least two patches; and
- computing the at least one slide-level tissue type according to the extracted geometrical features.

* * * * *